United States Patent
Lim et al.

(10) Patent No.: US 10,588,664 B2
(45) Date of Patent: Mar. 17, 2020

(54) SUBCUTANEOUS IMPLANT DELIVERY APPARATUS AND METHOD OF DELIVERING A SUBCUTANEOUS IMPLANTABLE DEVICE FOR ACCESSING A VASCULAR SITE

(71) Applicant: Agency for Science, Technology and Research, Singapore (SG)

(72) Inventors: Soo Ghim Lim, Singapore (SG); Ruey Feng Peh, Singapore (SG); Yee Han Kuan, Singapore (SG); Yanling Toh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 174 days.

(21) Appl. No.: 15/542,507

(22) PCT Filed: Dec. 28, 2015

(86) PCT No.: PCT/SG2015/050508
§ 371 (c)(1),
(2) Date: Jul. 10, 2017

(87) PCT Pub. No.: WO2016/111642
PCT Pub. Date: Jul. 14, 2016

(65) Prior Publication Data
US 2018/0264246 A1  Sep. 20, 2018

(30) Foreign Application Priority Data
Jan. 8, 2015 (SG) .............................. 10201500143S

(51) Int. Cl.
*A61B 17/34* (2006.01)
*A61B 17/04* (2006.01)
(Continued)

(52) U.S. Cl.
CPC .... *A61B 17/3468* (2013.01); *A61B 17/00234* (2013.01); *A61B 17/0482* (2013.01);
(Continued)

(58) Field of Classification Search
CPC ...... A61M 39/0208; A61M 2039/0223; A61M 2039/0232; A61M 37/0069; A61M 31/00; A61M 37/00; A61B 17/3468
See application file for complete search history.

(56) References Cited

U.S. PATENT DOCUMENTS

| 5,534,008 A | 7/1996 | Acksel |
| 8,348,882 B2 * | 1/2013 | Bardy ............... A61M 37/0069 604/57 |

(Continued)

FOREIGN PATENT DOCUMENTS

| WO | WO9933512 | 7/1999 |
| WO | WO2014017986 | 1/2014 |

OTHER PUBLICATIONS

Jennings, et al., The Venous Window Needle Guide, A Hemodialysis Cannulation Device for Salvage of Uncannulatable Arteriovenous Fistulas, 60 Journal of Vascular Surgery 1024 (2014).

*Primary Examiner* — Nathan R Price
*Assistant Examiner* — Melissa A Snyder
(74) *Attorney, Agent, or Firm* — K. David Crockett, Esq.; Niky Economy Syrengelas, Esq.; Crockett & Crockett, PC

(57) ABSTRACT

According to embodiments of the present invention, a subcutaneous implant delivery apparatus is provided. The apparatus includes a receiving portion configured to receive a subcutaneous implantable device; and a stabilizing portion configured to cooperate with the receiving portion to hold the subcutaneous implantable device in a fixed position. The receiving portion and the stabilizing portion are movable relative to each other between a released configuration, wherein the receiving portion and the stabilizing portion are
(Continued)

configured to move apart from each other to allow the receiving portion to be inserted under a skin layer, and a closed configuration, wherein the receiving portion and the stabilizing portion are configured to move toward each other to allow the subcutaneous implantable device to be held adjacent to the skin layer. According to further embodiments of the present invention, a method of delivering a subcutaneous implantable device for accessing a vascular site is also provided.

20 Claims, 12 Drawing Sheets

(51) Int. Cl.
*A61M 1/36* (2006.01)
*A61B 17/062* (2006.01)
*A61M 25/06* (2006.01)
*A61B 17/00* (2006.01)
*A61M 39/02* (2006.01)
*A61B 90/00* (2016.01)

(52) U.S. Cl.
CPC ......... *A61B 17/062* (2013.01); *A61M 1/3653* (2013.01); *A61M 1/3655* (2013.01); *A61M 25/06* (2013.01); *A61M 39/0208* (2013.01); *A61B 2017/00115* (2013.01); *A61B 2017/00876* (2013.01); *A61B 2017/047* (2013.01); *A61B 2017/0472* (2013.01); *A61B 2090/0811* (2016.02); *A61M 2039/0223* (2013.01); *A61M 2039/0232* (2013.01)

(56) References Cited

U.S. PATENT DOCUMENTS 8,398,654 B2   3/2013   Franklin et al.
2004/0199140 A1  10/2004   Rue et al.

* cited by examiner

SUBCUTANEOUS IMPLANT DELIVERY APPARATUS AND METHOD OF DELIVERING A SUBCUTANEOUS IMPLANTABLE DEVICE FOR ACCESSING A VASCULAR SITE

CROSS-REFERENCE TO RELATED APPLICATION

This application claims the benefit of priority of Singapore patent application No. 10201500143S, filed on 8 Jan. 2015, the content of it being hereby incorporated by reference in its entirety for all purposes.

TECHNICAL FIELD

Various embodiments relate to a subcutaneous implant delivery apparatus and a method of delivering a subcutaneous implantable device for accessing a vascular site.

BACKGROUND

End Stage Renal Disease (ESRD) is a debilitating and financially crippling chronic disease costing healthcare systems approximately a staggering $67 B annually to treat, with incidence growing at an unmanageable rate. Hemodialysis (HD) is the predominant choice of treatment for about 85% of ESRD patients. As much as 38% of a patient's HD expenditure may not be due to dialysis but rather, due to vascular access. Vascular access remains the Achilles heel and one of the biggest unmet needs of HD.

Currently, there are three ways to obtain HD vascular access. Arteriovenous fistula (AVF) remains the gold standard with the lowest risk of complications. An arteriovenous graft (AVG) is the second option with shorter lifespan and higher risk of complication. A central catheter (CC) is often the last resort, meant only for temporary use with risk of serious complications leading to mortality. As such, preserving the health of an AVF, reducing the use of AVGs and CCs and their associated surgeries, is one of the best strategies to reduce overall cost of ESRD.

Surveying the competitive landscape, there is a missing gap in innovations impacting AVF health at the "Wear & Tear" phase—the mid stage of an AVF lifespan after the stage where it is successfully created and matured, and before the stage of onset of deterioration requiring repair interventions. Impacting AVF health at the "Wear & Tear" stage addresses fundamental mechanisms to effectively preserve AVFs than salvage downstream effects. This is also the stage where most number of preventable complications occurs due to poor cannulation.

Thus, there is a need for a delivery device for easy implantation of a subcutaneous vascular access device under the skin, and above, though not in contact with an arteriovenous fistula (referred to as AV fistula or AVF).

SUMMARY

According to an embodiment, a subcutaneous implant delivery apparatus is provided. The subcutaneous implant delivery apparatus may include a receiving portion configured to receive a subcutaneous implantable device; and a stabilizing portion configured to cooperate with the receiving portion to hold the subcutaneous implantable device in a fixed position, wherein the receiving portion and the stabilizing portion are movable relative to each other between a released configuration and a closed configuration; wherein in the released configuration, the receiving portion and the stabilizing portion are configured to move apart from each other to allow the receiving portion to be inserted under a skin layer and the subcutaneous implantable device to be positioned subcutaneously; and wherein in the closed configuration, the receiving portion and the stabilizing portion are configured to move toward each other to allow the subcutaneous implantable device to be held adjacent to the skin layer, between the receiving portion and the stabilizing portion in the fixed position.

According to an embodiment, a method of delivering a subcutaneous implantable device for accessing a vascular site is provided. The method may include providing a subcutaneous implant delivery apparatus, according to various embodiments; receiving a subcutaneous implantable device on the receiving portion of the subcutaneous implant delivery apparatus; inserting the receiving portion under a skin layer; positioning the subcutaneous implantable device subcutaneously; holding the subcutaneous implantable device adjacent to the skin layer between the receiving portion and the stabilizing portion in a fixed position; releasing the subcutaneous implantable device by allowing the receiving portion and the stabilizing portion to move apart from each other; and removing the receiving portion from under the skin layer.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 6A shows a perspective view of a subcutaneous implant delivery device, in accordance with various embodiments, wherein the delivery device provides guided suturing, guided implant orientation test channels, and additional arteriovenous fistula (AV fistula) safety of a protection base plate, in accordance with various embodiments.

FIG. 6B shows a perspective view of the subcutaneous implant delivery device of FIG. 6A (without a handle) where a needle guide is positioned over a top handle of the subcutaneous implant delivery device of FIG. 6A, away from the area where a subcutaneous implant is being held, in accordance with various embodiments.

DETAILED DESCRIPTION

Figure 1A:
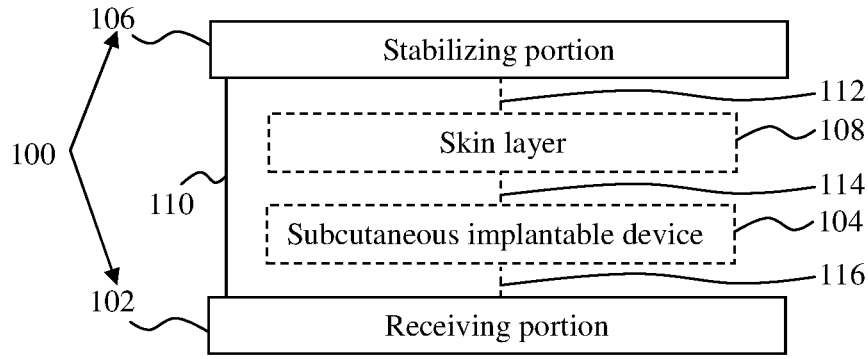
FIG. 1A shows a schematic cross-sectional view of a subcutaneous implant delivery apparatus, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments provide a delivery device for implantation of a subcutaneous implant.

The delivery device may provide stability and accuracy in positioning a vascular access device. The delivery device may further assist a user (or an operator) to properly anchor the access device to and from beneath the skin via sutures. The delivery device may also feature safety functions that may prevent the user from injuring the arteriovenous fistula (referred to as AV fistula or AVF) during the implantation process.

Various embodiments may provide an apparatus that stabilizes a subcutaneous implant (or a vascular access device or a subcutaneous implantable device) and guides a subcutaneous implant (or a vascular access device or a subcutaneous implantable device) to be implanted in the right orientation. The apparatus may include a base plate that holds the subcutaneous implant in place, and blocks erroneous suturing that may invade a target vessel. The apparatus may further include a suture mechanism that facilitates easy suturing of the subcutaneous implant onto the dermis layer of a subject's skin.

FIG. 1A shows a schematic cross-sectional view of a subcutaneous implant delivery apparatus 100, according to various embodiments. The subcutaneous implant delivery apparatus 100 includes a receiving portion 102 configured to receive a subcutaneous implantable device 104; and a stabilizing portion 106 configured to cooperate with the receiving portion 102 to hold the subcutaneous implantable device 104 in a fixed position, wherein the receiving portion 102 and the stabilizing portion 106 are movable relative to each other between a released configuration and a closed configuration; wherein in the released configuration, the receiving portion 102 and the stabilizing portion 106 are configured to move apart from each other to allow the receiving portion 102 to be inserted under a skin layer 108 and the subcutaneous implantable device 104 to be positioned subcutaneously; and wherein in the closed configuration, the receiving portion 102 and the stabilizing portion 106 are configured to move toward each other to allow the subcutaneous implantable device 104 to be held adjacent to the skin layer 108, between the receiving portion 102 and the stabilizing portion 106 in the fixed position.

In other words, the subcutaneous implant delivery apparatus 100 may include the receiving portion 102 and the stabilizing portion 106, coupled to each other, as represented by a line 110 so as to work in cooperation with each other. For example, the receiving portion 102 and the stabilizing portion 106 may be coupled mechanically via, but not limited to, a pivot point or a spring mechanism (not shown in FIG. 1A) so that the receiving portion 102 and the stabilizing portion 106 may move apart or move toward each other under different configurations. In some examples, the receiving portion 102 and the stabilizing portion 106 may be coupled to or attached to each other via a threadless press fit rod hinge (e.g., 686 of FIG. 6G). Using the threadless press fit rod hinge may advantageously reduce the risk of residual sterilization ethylene oxide (EtO) entrapment which occurs in screw threads. The stabilizing portion 106 and the receiving portion 102 may be complementary to each other. The receiving portion 102 may be shaped to receive or hold the subcutaneous implantable device 104, as represented by a dotted line 116. For example, the receiving portion 102 may include a recess in which the subcutaneous implantable device 104 or at least part thereof may be placed. The subcutaneous implantable device 104 or at least part thereof may be placed onto the receiving portion 102 when the subcutaneous implant delivery apparatus 100 is in the released configuration. The receiving portion 102, along with the subcutaneous implantable device 104 (which is received on the receiving portion 102) may be inserted under the skin layer 108, as represented by a dotted line 114, through an incision on the skin layer 108. The stabilizing portion 106 may remain above the skin layer 108. This means that the stabilizing portion 106 is a non-invasive part and is not inserted under the skin layer 108. In the closed configuration, the receiving portion 102 and the stabilizing portion 106 may be configured to move toward each other such that the stabilizing portion 106 may be in contact with the skin layer 108 (i.e., on the skin layer 108 or on the skin surface) or may be brought adjacent to the skin layer 108 (i.e., over the skin layer 108 or over the skin surface), as represented by a dotted line 112. At the same time, the subcutaneous implantable device 104 may move toward and may be brought in contact with underneath the skin layer 108. This way, the skin layer 108 and the subcutaneous implantable device 104 may be held in alignment (or sandwiched) between the receiving portion 102 and the stabilizing portion 106. In this closed configuration, the subcutaneous implantable device 104 being in contact with the skin layer 108 may be held firmly (non-movable) adjacent to the (underneath) skin layer 108, for example, by exerting an external compressing force onto the receiving portion 102 and the stabilizing portion 106 to allow the receiving portion 102 and the stabilizing portion 106 to move toward each other, thereby allowing temporarily locking of the subcutaneous implantable device 104 in place (in the fixed position).

In the context of various embodiments, the term "fixed position" may mean in an at least substantially non-movable and/or non-orientable state.

In the context of various embodiments, the term "adjacent to" may mean in contact with, or next to, or at least substantially near to.

The subcutaneous implant delivery apparatus 100 in accordance with various embodiments may allow implantation accuracy problems for the subcutaneous implantable device (e.g., 104) to be solved. It should be appreciated that implanting a subcutaneous device (e.g., 104), especially ones for accessing a blood vessel accurately, cannot afford to have position and/or orientation error, even though the error may be considered slight. In other words, there may be significantly low error tolerance (e.g., zero error tolerance). If a subcutaneous implantable device (e.g., 104) is placed at a wrong angle, or not directly above a vessel (vascular site), there may be a risk that a needle may not be able to accurately puncture the precise and consistent location of a target vessel. The subcutaneous implant delivery apparatus 100 in accordance with various embodiments may provide the following functions of temporarily locking the implant (e.g., 104) in place, checking the positional and angular accuracy of the implant (e.g., 104), and confirming/determining sutures catching the implant (e.g., 104) hidden under the skin (e.g., 108), all through real-time direct visualization. This may advantageously provide a cost-effective solution to the problems mentioned herein. Further, the integration of the aforesaid functions into one single apparatus (e.g., 100) may enable the problems mentioned herein to be solved without a need for sophisticated imaging technology despite the implant (e.g., 104) being hidden under the skin (e.g., 108).

In various embodiments, the receiving portion 102 and the stabilizing portion 106 may be movable relative to each other about a pivoting point.

In various embodiments, the subcutaneous implant delivery apparatus 100 may further include at least one position indicator configured to facilitate a visual indication of at least one of a position or an angular orientation of the subcutaneous implantable device 104 when received by the receiving portion 102 and held adjacent to the skin layer 108.

In various embodiments, the (at least one) position indicator may include a needle guide configured to receive a needle upon alignment of the subcutaneous implantable device 104 to at least one of a desired position or a desired angular orientation with respect to the receiving portion 102.

In other words, the position indicator may include a needle guide for determining the correct position and angular orientation of the subcutaneous implantable device 104.

In various embodiments, the needle guide may be configured to be coupled to the stabilizing portion 106 and activated by a rotation about a pivot positioned at a substantially mid-point of the stabilizing portion 106. The needle guide may rotate away from a plane of the stabilizing portion 106 and towards a plane perpendicular to the plane of the stabilizing portion 106 about the pivot. In reverse, the needle guide may rotate away from the plane perpendicular to the plane of the stabilizing portion 106 and towards the plane of the stabilizing portion 106 about the pivot. In other words, the needle guide may rotate in an upward-downward motion with respect to the plane of the stabilizing portion 106. An example of this needle guide activated by rotation about the pivot may be illustrated in FIGS. 6A to 6C.

In other embodiments, the needle guide may be configured to be coupled to the stabilizing portion 106 and activated by a swing rotation to move laterally along the stabilizing portion 106. The swing rotation may be about a pivot positioned at a distal end of the stabilizing portion 106. The swing rotation may be a side-to-side motion along the plane of the stabilizing portion 106 or along a plane parallel to the plane of the stabilizing portion 106 about the distal pivot. An example of this needle guide activated by swing rotation may be illustrated in FIGS. 6F and 6G. Having the needle guide activated by swing rotation may provide an advantage of not needing a locking mechanism (e.g., U-clamp 682 of FIG. 6F) to be removed and re-inserted when the needle is deployed through the needle guide, since the locking mechanism is not positioned overlying the needle guide or at least part of the needle guide (as compared to the example described in FIG. 6A).

In various embodiments, the subcutaneous implant delivery apparatus 100 may further include at least one anchor guide configured to facilitate the subcutaneous implantable device 104 to be anchored to the skin layer 108.

For example, the at least one anchor guide may include a suture guide marking.

In other words, various embodiments may provide the subcutaneous implant delivery apparatus 100 including: the receiving portion 102 configured to receive the subcutaneous implantable device 104; the stabilizing portion 106 to temporarily lock the subcutaneous implantable device 104 in a fixed position, wherein the receiving portion 102 and the stabilizing portion 106 are movable relative to each other between a released configuration and a closed configuration; wherein in the released configuration, the receiving portion 102 and the stabilizing portion 106 are moved apart from each other to allow the receiving portion 102 to be inserted under the skin layer 108 and the subcutaneous implantable device 104 to be positioned subcutaneously; and wherein in the closed configuration, the receiving portion 102 and the stabilizing portion 106 are moved toward each other to allow the implantable device 104 to be held firmly adjacent to the (underneath) skin layer 108, between the receiving portion 102 and the stabilizing portion 106; at least one (or a plurality of) position indicator(s) to visually confirm said implantable device 104 is in the correct position and/or orientation (angular orientation); and an or a plurality of anchor guide(s) to assist and visually confirm the implantable device 104 is correctly anchored to the skin 108.

In the context of various embodiments, the term "temporarily lock" may mean releasably secure, or lock/secure with a form of release mechanism. As a non-limiting example, the stabilizing portion 106 may temporarily lock the subcutaneous implantable device 104 via a continuous compressing force being applied between the stabilizing portion 106 and the receiving portion 102, or via a latching mechanism.

Other examples for "temporarily lock" may be in forms of a U-clamp with male and female interlocks, screw locks with rotational screw threads and magnetic locking mechanism to align and lock top and bottom shafts.

In the context of various embodiments, the term "held firmly" may mean held with an applied force, for example, to minimize or avoid movement.

In the context of various embodiments, the term "correct position and/or orientation" may mean a desired position and/or orientation (angular orientation) in accordance with medical professionals' practices. For example, the correct position and/or orientation in this context may refer to a position and/or orientation of the implantable device 104 under the skin 108, and above, though not in contact with an arteriovenous fistula.

The integration of various components of the subcutaneous implant delivery apparatus described herein, in accordance with various embodiments (e.g., 100) may create synergy that solves an implantation accuracy problem that existing vascular access devices may meet. This is because the subcutaneous implant delivery apparatus described herein, in accordance with various embodiments may solve a non-trivial problem of implanting a subcutaneous device (e.g., the subcutaneous implantable device 104) that cannot afford to have slight position and/or orientation (angular orientation) error. If the subcutaneous device (e.g., the subcutaneous implantable device 104), or may be referred to as a vascular access implant is placed at a slightly wrong (incorrect) angle, or not directly above a vessel, there runs the risk of a needle not being able to accurately puncture the precise and consistent location of the target vessel. The subcutaneous implant delivery apparatus described herein, in accordance with various embodiments, may combine the features of 'temporarily locking the implant (e.g., 104) in place', 'checking positional and angular accuracy', and 'confirming sutures catches the implant (e.g., 104) hidden under the skin (e.g., 108)' all through real-time direct visualization. The subcutaneous implant delivery apparatus described herein, in accordance with various embodiments is the most low cost solution to solve the non-trivial problem. It is believed that at least one of the combination/integration of the abovementioned three features into one device (e.g., 100), and the ability of the device (e.g., 100) to solve the problem without needing sophisticated imaging technology despite the implant (e.g., 104) being hidden under the skin (e.g., 108) constitutes a demonstration of an inventive effort.

In various embodiments, the receiving portion 102 may include a blocking base plate on which the subcutaneous implantable device 104 is to be placed, wherein the blocking base plate is configured to form a shield for an anatomy or a tissue underneath the subcutaneous implantable device 104.

In other words, the receiving portion 102 may include a blocking base plate on which tissue/blood vessels beneath the subcutaneous implantable device 104 is shielded. It should be appreciated that the blocking base plate is a safety feature to eradicate a possibility that a surgeon may accidentally pierce the vessel (vascular site) under the implant 104 (or any other tissue under the implant 104) during a procedure. The blocking base plate may also eradicate a possibility of the surgeon accidentally suturing the implant 104 together with the vessel, consequently risking the implant 104 compressing and causing stenosis on the vessel.

In particular, various embodiments may provide a subcutaneous implant delivery apparatus including: a receiving portion 102 configured to receive a subcutaneous implantable device 104; a stabilizing portion 106 configured to cooperate with the receiving portion 102 to hold the subcutaneous implantable device 104 in a fixed position; and a blocking base plate on which the subcutaneous implantable device 104 is to be placed, wherein the blocking base plate is configured to form a shield for an anatomy or a tissue underneath the subcutaneous implantable device 104, wherein the receiving portion and the stabilizing portion are movable relative to each other between a released configuration and a closed configuration; wherein in the released configuration, the receiving portion and the stabilizing portion are configured to move apart from each other to allow the receiving portion to be inserted under a skin layer and the subcutaneous implantable device to be positioned subcutaneously; and wherein in the closed configuration, the receiving portion and the stabilizing portion are configured to move toward each other to allow the subcutaneous implantable device to be held adjacent to the skin layer, between the receiving portion and the stabilizing portion in the fixed position. The receiving portion 102 may include the blocking base plate.

In various embodiments, the receiving portion 102 may include a releasable attachment mechanism to which the subcutaneous implantable device 104 is to be releasably attached. For example, the releasable attachment mechanism may include a clamp. In another example, the releasable attachment mechanism may include a retaining clip.

In various embodiments, the subcutaneous implant delivery apparatus 100 may further include a handle extending from at least one of the receiving portion 102 or the stabilizing portion 106.

The handle may form part of the at least one of the receiving portion 102 or the stabilizing portion 106. In other words, the handle may be an integral part of the at least one of the receiving portion 102 or the stabilizing portion 106. Alternatively, the handle may be a separate part that may be coupled or attached to the at least one of the receiving portion 102 or the stabilizing portion 106.

In other embodiments, the subcutaneous implant delivery apparatus 100 may further include a handle extending from each of the receiving portion 102 and the stabilizing portion 106.

The handle may form part of each of the receiving portion 102 and the stabilizing portion 106. In other words, the handle may be an integral part of each of the receiving portion 102 and the stabilizing portion 106. Alternatively, the handle may be a separate part that may be coupled or attached to each of the receiving portion 102 and the stabilizing portion 106.

In various embodiments, the handle(s) may be made of plastic. Generally, the handle(s) may be made of any material suitable for facilitating holding of a hand-held device (e.g., the subcutaneous implant delivery apparatus 100) and for sterile use (e.g., to facilitate or for surgery purpose).

In various embodiments, the handles may be configured to move toward each other upon exerting an external force thereon to correspondingly allow the receiving portion 102 and the stabilizing portion 106 to be moveable toward each other in the closed configuration.

In various embodiments, the handle or the handles may be dimensioned and/or shaped in a manner to allow for at least one of a reduction in the weight of the subcutaneous implant delivery apparatus 100, an improved balance and/or user comfort in handling the subcutaneous implant delivery apparatus 100, and a reduction in manufacturing cost of the subcutaneous implant delivery apparatus 100.

In various embodiments, the subcutaneous implant delivery apparatus 100 may further include at least one needle arranged to self suture through the subcutaneous implantable device 104 when received by the receiving portion 102, to the skin layer 108 upon moving the receiving portion 102 and the stabilizing portion 106 toward each other.

In other words, the apparatus 100 may further include needles that self sutures through the subcutaneous implantable device 104 in the receiving portion 102, to the skin 108 upon moving the receiving portion 102 and the stabilizing portion 106 closer to each other.

In the context of various embodiments, the term "self suture" may mean a capability of performing suturing without a user's direct influence. In other words, "self suture" in this context is different from a user using a needle to perform suturing.

For example, in this case, by moving the receiving portion 102 and the stabilizing portion 106 closer to each other, the at least one needle (or the needles) is able to perform suturing (on its own) without a user manually operating (holding, pushing, or pulling) the at least one needle (or the needles).

In various embodiments, the receiving portion 102 and the stabilizing portion 106 may be made of a material selected from plastic, austenitic molybdenum-containing stainless steel, and medical grade titanium. For example, the receiving portion 102 may be made of a material same as that for the stabilizing portion 106. In other examples, the receiving portion 102 may be made of a material different from that for the stabilizing portion 106. Generally, each of the receiving portion 102 and the stabilizing portion 106 may be made of any other rigid material suitable for sterile use (e.g., to facilitate or for surgery purpose).

In various embodiments, the subcutaneous implant delivery apparatus 100 may further include a locking mechanism arranged to releasably lock the receiving portion 102 and the stabilizing portion 106 in the closed configuration.

Each of the receiving portion 102 and the stabilizing portion 106 may include a screw hole, and the locking mechanism may include a screw arranged through the screw holes.

For example, the locking mechanism may include a U-lock (or a U-shaped lock) or a U-clamp.

In various embodiments, the receiving portion 102 may include a groove for receiving the locking mechanism (e.g., U-clamp 682 of FIG. 6F) such that the locking mechanism may be flushed with a bottom surface of the receiving portion 102 to prevent skin from being pinched when the locking mechanism is engaged to temporarily lock the stabilizing portion 106 and the receiving portion 102 together.

Figure 1B:
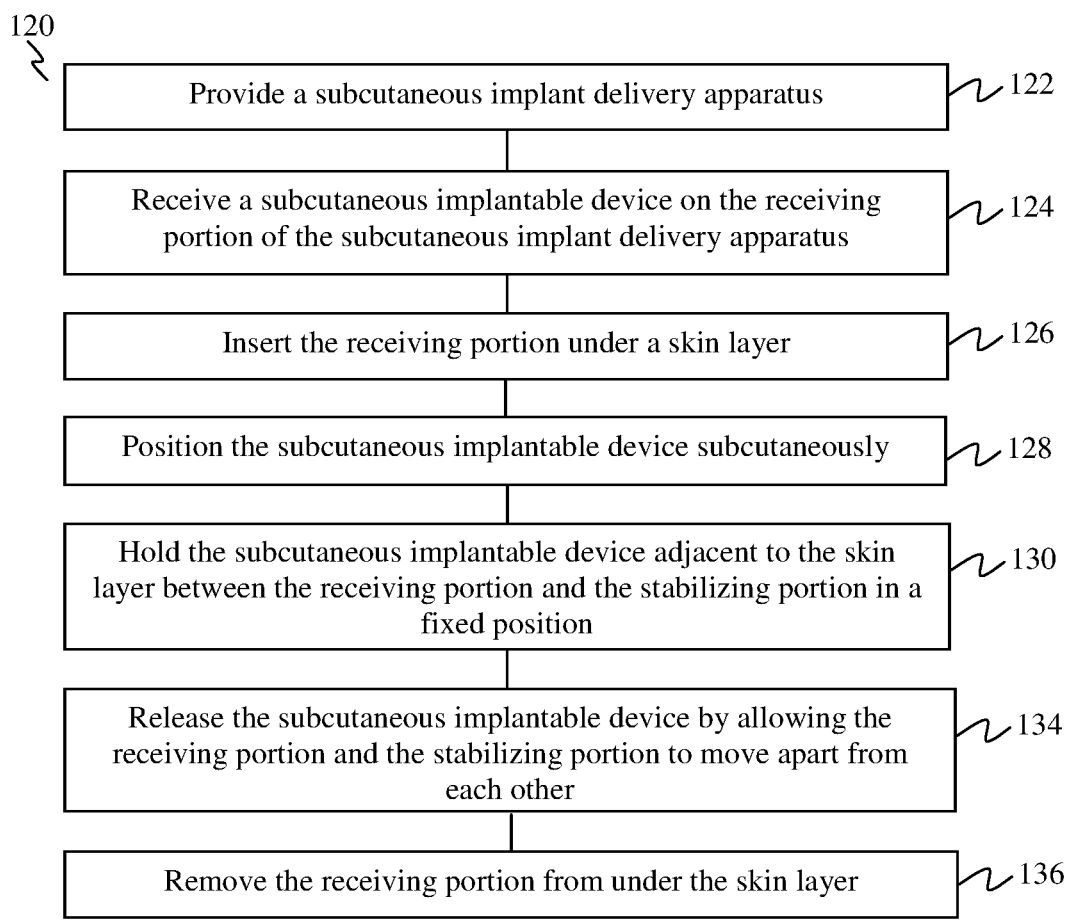
FIG. 1B shows a flow chart illustrating a method of delivering a subcutaneous implantable device for accessing a vascular site, according to various embodiments.

FIG. 1B shows a flow chart illustrating a method 120 of delivering a subcutaneous implantable device for accessing a vascular site, according to various embodiments. The subcutaneous implantable device may be described in the same or similar context with the subcutaneous implantable device 104 of FIG. 1A. At 122, a subcutaneous implant delivery apparatus as herein described (e.g., 100 of FIG. 1A) may be provided. At 124, a subcutaneous implantable device (e.g., 104) may be received on the receiving portion 102 of the subcutaneous implant delivery apparatus 100. At 126, the receiving portion 102 may be inserted under a skin layer (e.g., 108 of FIG. 1A). At 128, the subcutaneous implantable device 104 may be positioned subcutaneously. At 130, the subcutaneous implantable device 104 may be held adjacent to the skin layer 108 between the receiving portion 102 and the stabilizing portion 106 in a fixed position. At 134, the subcutaneous implantable device 104 may be released by allowing the receiving portion 102 and the stabilizing portion 106 to move apart from each other. At 136, the receiving portion 102 may be removed from under the skin layer 108.

In various embodiments, the subcutaneous implantable device 104 may be sutured to the skin layer 108 in the fixed position, for example, prior to the step 134. In this case, the sutured subcutaneous implantable device 104 may be released by allowing the receiving portion 102 and the stabilizing portion 106 to move apart from each other.

In other words, the method 120 of delivering the subcutaneous implantable device (e.g., 104) for accessing a vascular site, according to various embodiments may include placing the subcutaneous implantable device 104 onto the receiving portion 102 of the subcutaneous implant delivery apparatus 100, and inserting the receiving portion 102, along with the subcutaneous implantable device 104 (which is received on the receiving portion 102) under the skin layer 108 through an incision on the skin layer 108 to position the subcutaneous implantable device 104 subcutaneously. With the stabilizing portion 106 of the subcutaneous implant delivery apparatus 100 remaining above the skin layer 108, the method 102 may further include moving the receiving portion 102 and the stabilizing portion 106 toward each other, for example, by exerting an external compressing force onto the receiving portion 102 and the stabilizing portion 106, such that the stabilizing portion 106 may be in contact with the skin layer 108 (i.e., on the skin layer 108 or on the skin surface) or may be brought adjacent to the skin layer 108 (i.e., over the skin layer 108 or over the skin surface). At the same time, the method 102 may include moving the subcutaneous implantable device 104 toward and brought in contact with underneath the skin layer 108, allowing the skin layer 108 and the subcutaneous implantable device 104 to be held in alignment (or sandwiched) between the receiving portion 102 and the stabilizing portion 106. This allows temporarily locking of the subcutaneous implantable device 104 in place (in the fixed position). With the subcutaneous implantable device 104 held in the fixed position with respect to the (underneath) skin layer 108 by the subcutaneous implant delivery apparatus 100, the method 102 may include suturing the subcutaneous implantable device 104 to the skin layer 108 so as to secure the subcutaneous implantable device 104 to the skin layer 108 in the fixed position. The subcutaneous implant delivery apparatus 100 may then be removed in its entirety by allowing the receiving portion 102 and the stabilizing portion 106 to move apart from each other, for example, by removing the applied compressing force or by releasing a releasable locking of the receiving portion 102 and the stabilizing portion 106 in the closed configuration, to release the sutured subcutaneous implantable device 104 from the receiving portion 102 and to remove the receiving portion 102 from under the skin layer 108 through the incision.

While the method described above is illustrated and described as a series of steps or events, it will be appreciated that any ordering of such steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

The subcutaneous implantable device and the subcutaneous implant delivery apparatus (as described in FIG. 1B) may include the same or like elements or components as those of the subcutaneous implantable device 104 and the subcutaneous implant delivery apparatus 100 of FIG. 1A, respectively, and as such, the same numerals are assigned and the like elements may be as described in the context of the subcutaneous implantable device 104 and the subcutaneous implant delivery apparatus 100 of FIG. 1A, and therefore the corresponding descriptions are omitted here.

In various embodiments, the method 120 may further include facilitating a visual indication of at least one of a position or an angular orientation of the subcutaneous implantable device 104 when received by the receiving portion 102 and held adjacent to the skin layer 108.

For example, the step of facilitating the visual indication may include providing a needle guide for receiving a needle upon alignment of the subcutaneous implantable device 104 to at least one of a desired position or a desired angular orientation with respect to the receiving portion 102.

In various embodiments, the method 120 may further include facilitating the subcutaneous implantable device 104 to be anchored to the skin layer 108.

In various embodiments, the method 120 may further include providing or forming a shield for an anatomy or a tissue underneath the subcutaneous implantable device 104. For example, the method 120 may include providing a blocking base plate on which the subcutaneous implantable device is to be placed to form a shield for an anatomy or a tissue underneath the subcutaneous implantable device. The receiving portion may include the blocking base plate. In other words, the method 120 may provide implanting the subcutaneous implantable device 104 (or any device) above a vein subcutaneously in a safe way with the blocking base plate shielding the vein.

In particular, various embodiments may provide a method of delivering a subcutaneous implantable device for accessing a vascular site, the method including: providing a subcutaneous implant delivery apparatus as herein described (e.g., 100 of FIG. 1A); receiving a subcutaneous implantable device (e.g., 104) on the receiving portion 102 of the subcutaneous implant delivery apparatus 100; providing a blocking base plate on which the subcutaneous implantable device 104 is to be placed to form a shield for an anatomy or a tissue underneath the subcutaneous implantable device 104; inserting the receiving portion 102 under a skin layer (e.g., 108 of FIG. 1A); positioning the subcutaneous implantable device 104 subcutaneously; holding the subcutaneous implantable device 104 adjacent to the skin layer 108 between the receiving portion 102 and the stabilizing portion 106 in a fixed position; releasing the subcutaneous implantable device 104 by allowing the receiving portion 102 and the stabilizing portion 106 to move apart from each other; and removing the receiving portion 102 from under the skin layer 108.

In various embodiments, the method 120 may further include providing a handle extending from each of the receiving portion 102 and the stabilizing portion 106, and moving the handles toward each other upon exerting an external force thereon to correspondingly allow the receiving portion 102 and the stabilizing portion 106 to be moveable toward each other in the closed configuration.

In various embodiments, the method 120 may further include self suturing through the subcutaneous implantable device 104 when received by the receiving portion 102, to the skin layer 108 upon moving the receiving portion 102 and the stabilizing portion 106 toward each other.

In various embodiments, the method 120 may further include releasably locking the receiving portion 102 and the stabilizing portion 106 in the closed configuration.

Examples of the subcutaneous implant delivery apparatus in accordance with various embodiments and the method of of delivering a subcutaneous implantable device for accessing a vascular site, according to various embodiments will be described as follow.

Figure 2A:
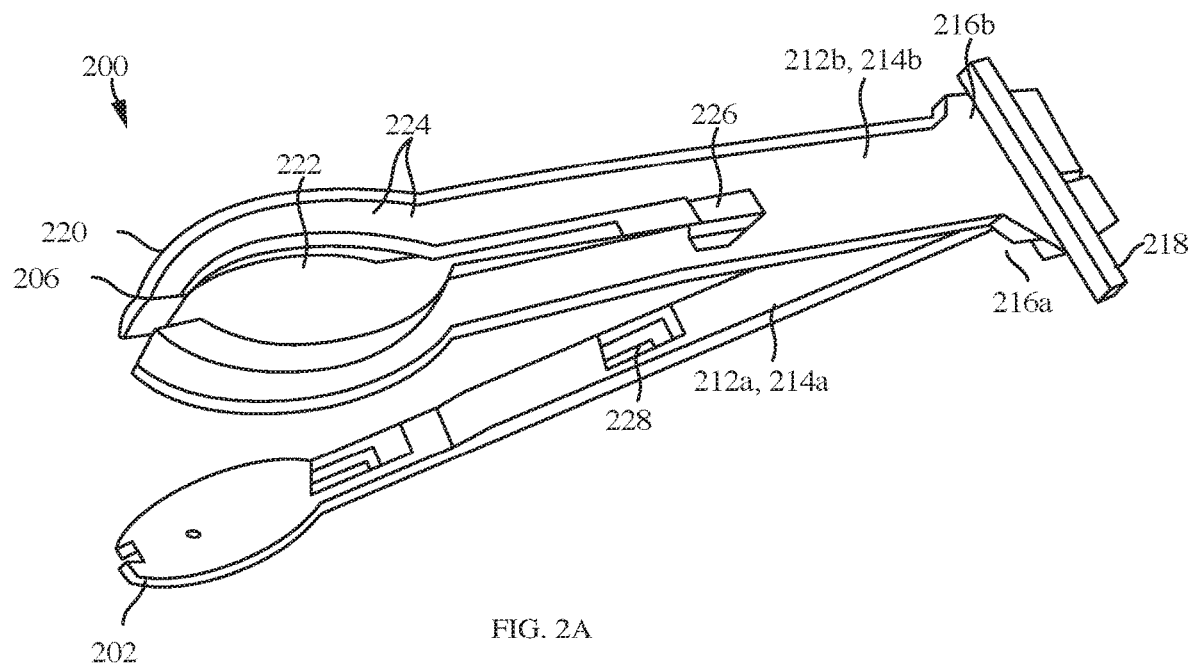
FIG. 2A shows a perspective view of a simplified version of a delivery device for implantation of a subcutaneous implant, in accordance with various embodiments.

FIG. 2A shows a perspective view of a simplified version of a delivery device 200 for implantation of a subcutaneous implant (not shown), in accordance with various embodiments. For example, the delivery device 200 may be a simplified subcutaneous implant delivery device. The delivery device 200 and the subcutaneous implant may include the same or like elements or components as those of the subcutaneous implant delivery apparatus 100 and the subcutaneous implantable device 104 of FIG. 1A, respectively, and as such, the same numerals are assigned and the like elements may be as described in the context of the subcutaneous implant delivery apparatus 100 and the subcutaneous implantable device 104 of FIG. 1A, and therefore the corresponding descriptions may be omitted here.

Figure 2B:
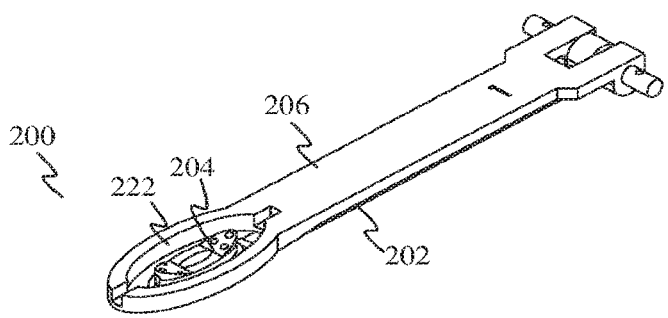
FIGS. 2B and 2C respectively show a perspective view and a plan view of the delivery device of FIG. 2A in a closed configuration, in accordance with various embodiments.
Figure 2C:
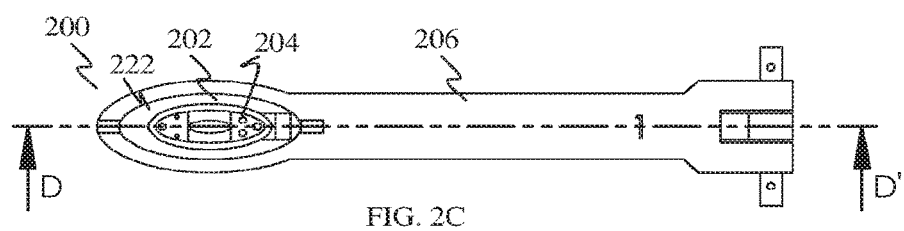

FIGS. 2B and 2C respectively show a perspective view and a plan view of the delivery device 200 in a closed configuration, in accordance with various embodiments.

As seen in FIG. 2A, the device 200 may include (i) a spoon-shaped bottom holder member 202 designed to hold a subcutaneous implant (not shown in FIG. 2A) and insertable into a limited space within a subcutaneous tissue (not shown in FIG. 2A); (ii) a top stabilizer member 206 designed to be pressed down above the skin (not shown in FIG. 2A) to secure the subcutaneous implant, that may be held by the spoon-shaped bottom holder member 202, temporarily in a fixed position under and against the skin; and (iii) a handle member 212*a*, 212*b*, each connecting the bottom holder 202 and the top stabilizer 206 proximally to each other to form respective shaft 214a, 214b. A free end 216a, 216b of each of the respective shaft 214a, 214b may be movably hinged together, for example, via a hinging element 218 (e.g., a pivoting point or a pivot). The device 200 as shown in FIG. 2A is in a released (or open) configuration. The spoon-shaped bottom holder member 202 and the top stabilizer member 206 of the delivery device 200 may operate like a pair of tongs.

The spoon-shaped bottom holder member 202 and the top stabilizer member 206 of FIG. 2A may include the same or like elements or components as those of the receiving portion 102 and the stabilizing portion 106 of FIG. 1A, respectively, and as such, the same numerals are assigned and the like elements may be as described in the context of the the receiving portion 102 and the and the stabilizing portion 106 of FIG. 1A, and therefore the corresponding descriptions may be omitted here.

The distal end 220 of the top stabilizer 206 has a gap 222 designed to allow the top handle 212b to expand flexibly based on the thickness of the skin.

There may be groove markers 224 on the top stabilizer 206 to guide suture needles (not shown in FIG. 2A) to find or local both the proximal and distal ends of the subcutaneous implant when the subcutaneous implant is hidden under the skin, and then to suture through the implant to anchor against the skin.

The handle 212a, 212b may be configured to allow the two shafts 214a, 214b to be hinged and aligned adjacent and parallel to each other to allow an operator to hold on to the delivery device 200.

The top stabilizer 206 and the spoon-shaped bottom holder 202 may be configured to have a protrusion 226 and an indentation 228 (complementary to the protrusion 226), respectively, to allow the two parts 206, 202 to be aligned properly during closure (as seen in FIG. 2B), where a central longitudinal axis of the top stabilizer 206 and a central longitudinal axis of the spoon-shaped bottom holder 202 may be in alignment with each other along a line D-D' of FIG. 2C. In another example (not shown here), the top stabilizer 206 and the spoon-shaped bottom holder 202 may be configured to have an indentation and a protrusion (complementary to the indentation), respectively, to allow the two parts 206, 202 to be aligned properly during closure. Other possible alternatives to achieve "proper alignment" of the two parts 206, 202 may be by using electronic touch sensors with light emitting diode (LED) indicators that lights up when the top shaft 214b and the bottom shaft 214a are aligned properly. Alternate to the LED indicators, an alarm system may also be used to confirm that the top shaft 214b and the bottom shaft 214a are aligned properly, e.g., via "beep" alarms. Yet another variation to the LED indicators may be the use of magnetic locking mechanisms that align and lock the top and bottom shafts 214b, 214a respectively.

A subcutaneous implant 204 may be positioned within or in alignment with a circumferential peripheral of the gap 222 as seen in FIGS. 2B and 2C. The subcutaneous implant 204 may be described in the same or similar context with the subcutaneous implantable device 104 of FIG. 1A.

FIGS. 3A to 3H show diagrams illustrating a method of utilizing the simplified delivery device 200 of FIG. 2A to implant a subcutaneous implant, such as a vascular access device for arteriovenous fistula (AVF or AV fistula).

Figure 3A:
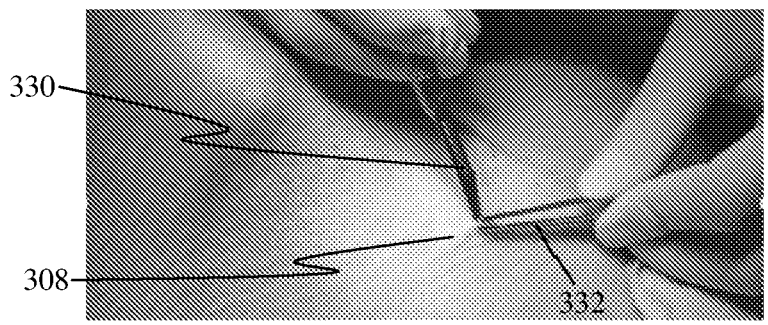
FIGS. 3A to 3H show diagrams illustrating a method of utilizing the simplified delivery device of FIG. 2A to implant a subcutaneous implant, such as a vascular access device for arteriovenous fistula (AVF or AV fistula), in accordance with various embodiments.

As seen in FIG. 3A which illustrates creating an incision, a cut down incision between about 1 cm to about 3 cm long may be created on a skin 308. The incision may be created using a surgical knife 330. A forcep or tweezer 332 may be used to hold onto the skin 308 during the incision procedure. The incision may allow access to a space below the dermis and a thin layer of subcutaneous tissue. A tunnel along the subcutaneous tissue under the skin 308 may be created. The tunnel may be about 2-3 mm below the top surface of the skin 308 (or about 1 mm below the bottom layer of the skin 308), running parallel with the AV fistula (not shown) in a longitudinal direction.

Figure 3B:
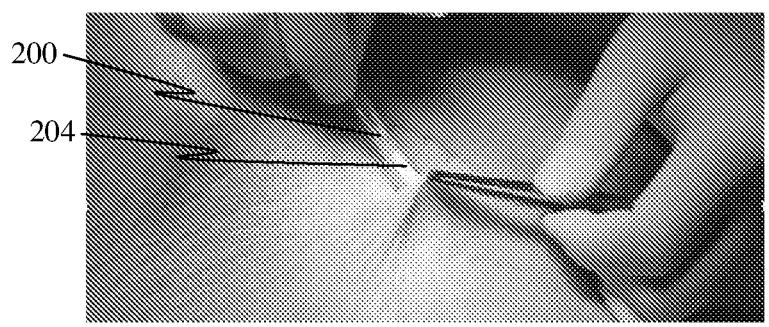
Figure 3C:
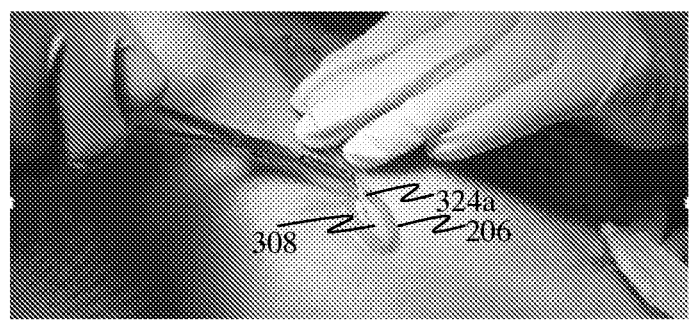

As seen in FIG. 3B (which illustrates insertion of an implant 204) and FIG. 3C (which illustrates suturing a proximal end of the implant 204 to the skin 308), an access device (e.g., the subcutaneous implant 204 of FIGS. 2B and 2C) may be inserted using the delivery device 200 into the incision created, and slipped along and into the subcutaneous tissue tunnel in the longitudinal direction parallel with the AV fistula. The depth of insertion may depend on the incision created or at the depth as indicated on the delivery device 200. The top stabilizer 206 of the delivery device 200 may close in a downward direction and may hold on to the skin 308 and the access device 204 (that is hidden underneath the skin 308) firmly. The proximal end of the access device 204 may be sutured onto the skin 308. The location of suture may be guided by a landmark groove 324a shown at the proximal end of the top stabilizer 206. As seen in FIG. 3C, suturing may be performed manually.

Figure 3D:
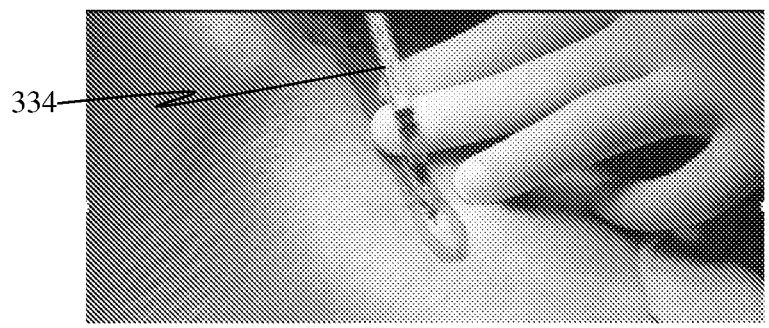

The orientation of the access device 204 may be confirmed by using a test needle 334, which may be smaller in size than a typical dialysis needle (such as 21 G to 25 G), to access the AV fistula, as seen in FIG. 3D (which illustrates confirmation of implant orientation via flash back of the test needle 334). The device orientation may be confirmed upon seeing blood flash back in the test needle 334.

Figure 3E:

As seen in FIG. 3E (which illustrates application of pressure for hemostasis), after the test needle 334 (or may be referred to as a guiding needle) is removed, a small amount of pressure may be applied at the access device area briefly to ensure hemostasis of the AV fistula as per a typical medical professional (e.g., nurse) workflow.

Figure 3F:
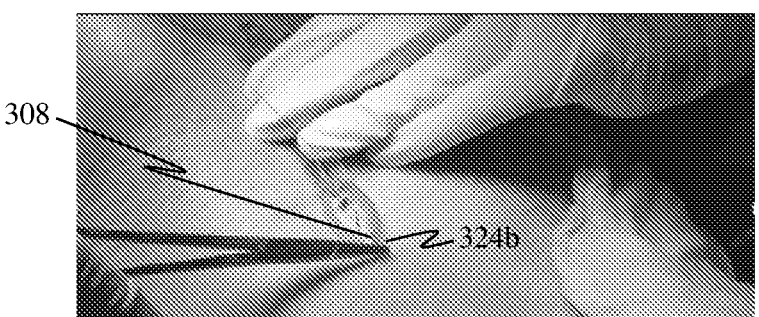

Upon confirmation of the orientation of the device 204, the distal end (or remaining suture ports) of the device 204 may be sutured onto the skin 308, as seen in FIG. 3F (which illustrates suturing of distal end of the implant 204 to the skin 308). The location of suture may be guided by a landmark groove 324b shown at the distal end of the top stabilizer 206.

Figure 3G:
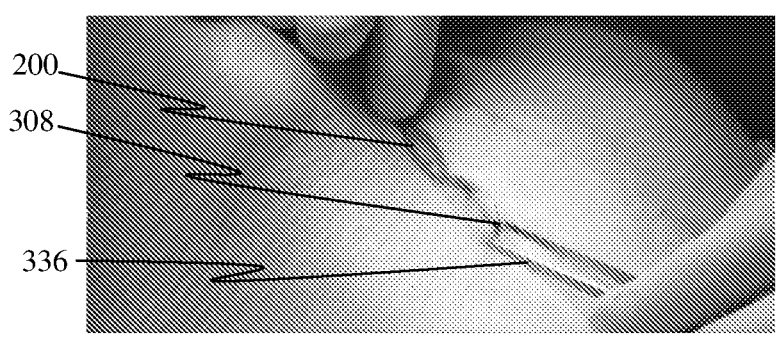

As seen in FIG. 3G which illustrates the removal of the delivery device 200, the skin 308 on top of the distal end of the access device 204 may be held by a tool 336 (e.g., a forcep or tweezer) and the delivery device 200 may be removed by depressing slightly.

Figure 3H:
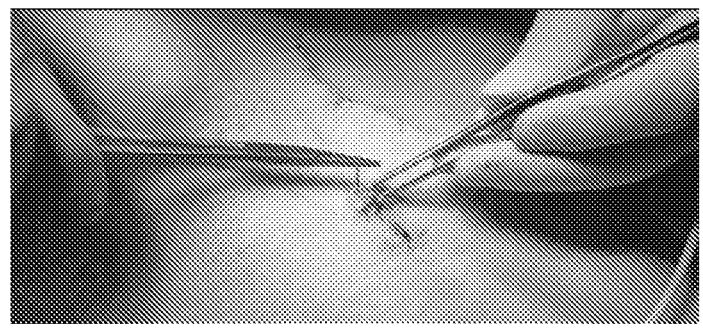

As seen in FIG. 3H (where the incision site is sutured close), the incision site may be sutured closed after the procedure (method) for healing. Dialysis may be commenced after about 5-14 days, after the implant 204 is encapsulated by its surrounding subcutaneous tissue. The skin sutures may be removed at this point if the operator wishes to. Dialysis may include inserting a needle through the access device 204 to a vascular site. Once dialysis is completed, the needle may be removed and pressure may be applied on the area to achieve hemostasis as per usual work protocol.

Figure 4A:
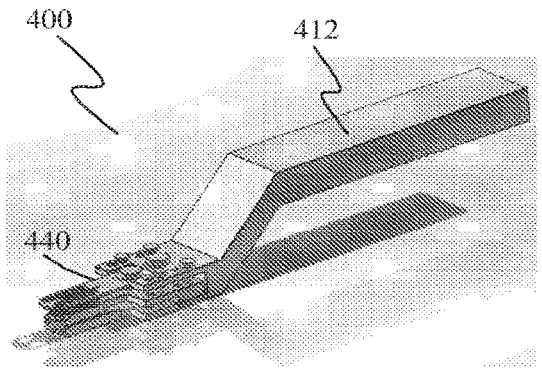
FIG. 4A shows a perspective view of a self-suturing delivery device for implantation of a subcutaneous implant, in accordance with various embodiments.
Figure 4B:
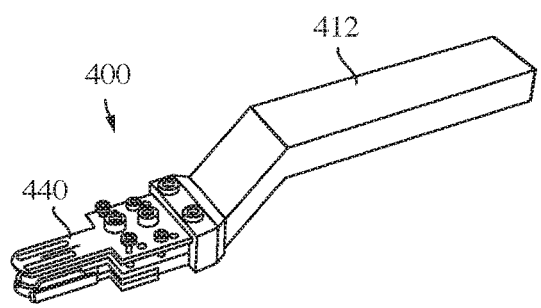
FIG. 4B shows a photograph illustrating a prototype realization of the self-suturing delivery device of FIG. 4A, in accordance with various embodiments.
Figure 4C:
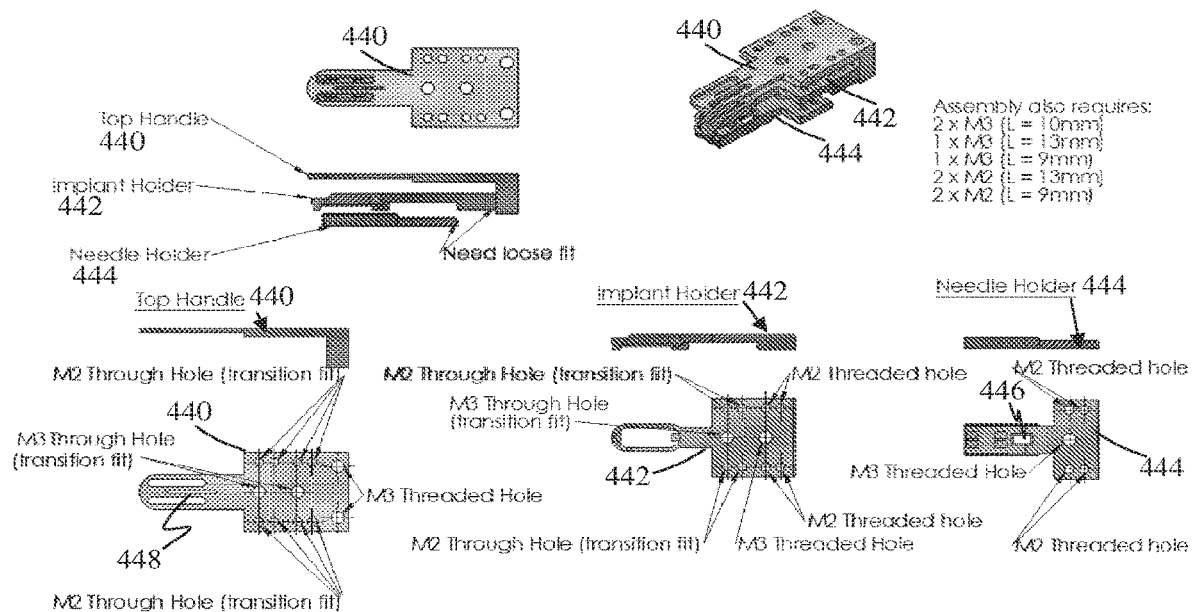
FIG. 4C shows schematic drawings (plan view, side view, and perspective view) illustrating the self-suturing delivery device of FIG. 4A and its components, in accordance with various embodiments.

FIG. 4A shows a perspective view of a self-suturing delivery device 400 for implantation of a subcutaneous implant (not shown), in accordance with various embodiments. For example, the self-suturing device 400 may be a subcutaneous implant delivery device with self suturing mechanisms. FIG. 4B shows a photograph illustrating a prototype realization of the self-suturing delivery device 400 of FIG. 4A. FIG. 4C shows schematic drawings (plan view, side view, and perspective view) illustrating the self-suturing delivery device 400 of FIG. 4A and its components. For example, the self-suturing delivery device 400 and the subcutaneous implant may include the same or like elements or components as those of the subcutaneous implant delivery apparatus 100 and the subcutaneous implantable device 104 of FIG. 1A, respectively, and as such, the same numerals are assigned and the like elements may be as described in the context of the subcutaneous implant delivery apparatus 100 and the subcutaneous implantable device 104 of FIG. 1A, and therefore the corresponding descriptions may be omitted here.

As seen in FIGS. 4A to 4C, the delivery device 400 may include (i) a top handle metal member 440 (e.g., stainless steel S316 or medical grade titanium) which may be connected to a handle 412. The handle may be made from a different material (e.g., hard plastics like polyvinyl chloride (PVC), acrylonitrile butadiene styrene (ABS), or polycarbonate). The delivery device 400 may include (ii) an implant holder member 442 that acts as a base to hold an implantable device (e.g., the subcutaneous implant). The implant holder 442 may be held in place by a combination of fixed and moveable screws (e.g., positions of which may be as indicated by M2 and/or M3 through holes or threaded holes). The fixed screws may hold the implant holder 442 and the top handle 440 in place, while the moveable screw may allow the implant holder 442 to be moveable upwards to close the gap between the top handle 440 and the implant holder 442.

For example, the implant holder member 442 and the top handle 440 may include the same or like elements or components as those of the receiving portion 102 and the stabilizing portion 106 of the subcutaneous implant delivery apparatus 100 of FIG. 1A, respectively, and therefore the corresponding descriptions may be omitted here.

The delivery device 400 may further include (iii) a needle holder member 444, that may be placed below the implant holder 442, used for holding a plurality of straight needles (not shown in FIGS. 4A to 4C) loaded with sutures in place. The needle holder 444 has a slit 446 to align sutures properly. The needle holder 444 may be secured to the top handle 440 with a combination of fixed and moveable screws (e.g., positions of which may be as indicated by M2 and/or M3 through holes or threaded holes). The fixed screws may hold the needle holder 444 and the top handle 440 in place, while the moveable screw may allow the needle holder 444 to be moveable upwards to close the gap between the needle holder 440 and the implant holder 442. The needle holder 440 and the implant holder 442 may be loosely fitted to each other. The delivery device 400 may include (iv) the handle member 412 that allows the operator to hold on to the delivery device 400.

The top handle member 440 may include a long slit 448 in the center to guide a small test needle, e.g., sized 21 G-25 G, to access a vasculature below the implant (or implantable) device (e.g., the subcutaneous implantable device 104 of FIG. 1A) to confirm that the implantable device is correctly positioned and orientated above the vasculature.

There may be needles and sutures of sufficient lengths (about 4 sets of sutures with 8 needles) held by the needle holder 444. For example, the needle length may be between about 4 mm to about 17 mm. The suture length may be between about 15 mm to about 30 mm.

The needles, upon moving the needle holder 444 upwards, may trigger the needles to travel through the implantable device, piercing through the skin above the delivery device 400, and emerge from the top handle 440.

Movements of the implant holder 442 and the needle holder 444 may be made manually by the operator turning the screw threads, or by an electro-motor mechanism that may be incorporated to the delivery device 400.

The top handle 440 and the implant holder 442 when fully closed by the screw thread levers, may be configured to have a gap inbetween. This may be so to ensure that the skin and the subcutaneous tissue over the implantable device is not overly compressed, especially during the procedure when the top handle 440 may be required to close down to clamp on the skin to lock the implantable device in position.

The distal end of the implant holder 442 may also be configured to include a lowered step for holding the implant device in place (not shown), but yet may allow for easy removal of the delivery device 400 once the implant device is sutured onto the skin.

FIGS. 5A to 5G show diagrams illustrating a method of utilizing the self-suturing delivery device 400 of FIG. 4A to implant a subcutaneous implant, such as a vascular access device for AV fistula.

Figure 5A:
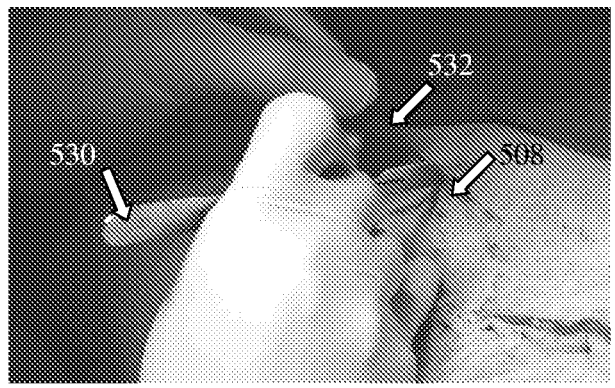
FIGS. 5A to 5G show diagrams illustrating a method of utilizing the self-suturing delivery device of FIG. 4A to implant a subcutaneous implant, such as a vascular access device for arteriovenous fistula (AVF or AV fistula), in accordance with various embodiments.

As seen in FIG. 5A which illustrates creation of cut down incision, a cut down incision between about 1 cm to about 3 cm long may be created on a skin 508. The incision may be created using a surgical knife 530. A forcep or tweezer 532 may be used to hold onto the skin 508 during the incision procedure. The incision may allow access to a space below the dermis and a thin layer of subcutaneous tissue. A tunnel along the subcutaneous tissue under the skin 508 may be created. The tunnel may be about 2-3 mm below the top layer of the skin 508 (or about 1 mm below the bottom layer of the skin 508), running parallel with the AV fistula (not shown) in a longitudinal direction.

Figure 5B:
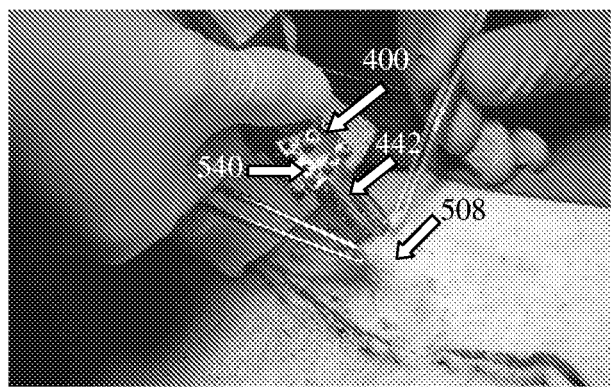

As seen in FIG. 5B (which illustrates insertion of the self-suturing delivery device 400 and tightening of implant holder 442 to secure the delivery device 400 with the skin 508), an access device (e.g., the subcutaneous implantable device 104 of FIG. 1A) may be inserted using the delivery device 400 into the incision created, and slipped along and into the subcutaneous tissue tunnel in the longitudinal direction parallel with the AVF. The depth of insertion may depend on the incision created or at the depth as indicated by the delivery device 400. Insertion of the self-suturing delivery device 400 and tightening of screw 540 at the implant holder 442 to move the access device 104 (that is hidden underneath the skin 508) upward and secure said device 104 in position against the skin 508 and the subcutaneous tissue above the device 104.

Figure 5C:
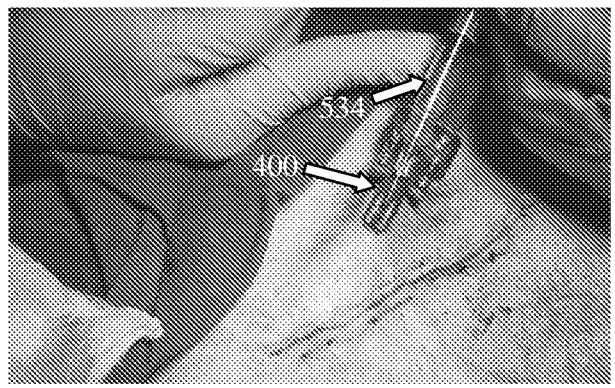

The orientation of the access device 104 may be confirmed by using a test needle 534, which may be smaller in size than a typical dialysis needle (such as 21 G to 25 G), to access the AV fistula, as seen in FIG. 5C (which illustrates confirmation of implant orientation with small test needle 534). The device orientation may be confirmed upon seeing blood flash back in the test needle 534.

Figure 5D:
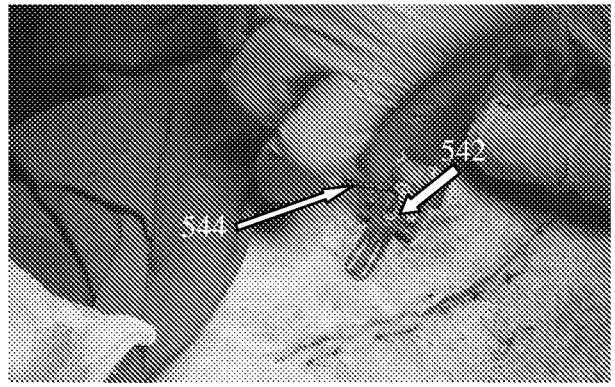

As seen in FIG. 5D (which illustrates tightening of needle holder plates 444 to trigger suture needles pre-loaded in the implant 104 and the delivery device 400), a second screw 542 connected to the needle holder 444 (that is hidden underneath the skin 508) may be tightened to trigger the suture needles (not shown in FIG. 5D) pre-loaded in the implant 104 and the delivery device 400. For example, tightening of the second screw 542 may be carried out using an alien key 544. The suture needles, upon trigger by the needle holder 444, may move upwards and automatically pierce through the skin 508 from beneath the needle holder 444. This way, self-suturing may be performed and this is different to the manual suturing as described in FIGS. 3C and 3F.

Figure 5E:
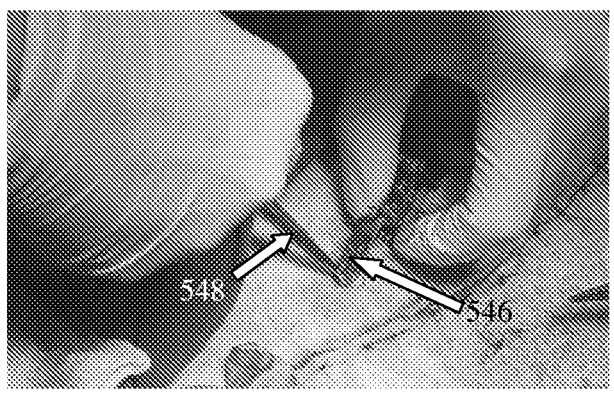

As seen in FIG. 5E (which illustrates retrieval of needles 546 that is fired through and from below the skin 508, securing sutures to anchor the implant 104 to the skin 508), needles 546 may be retrieved from the implant 104 (that is hidden underneath the skin 508) by means of grabbing and pulling the needle tip exposed from the skin 508. For example, the needle tip may be grabbed by a forcep or tweezer 548. In this case, the sutures may be secured firmly for all four pairs of sutures to anchor the implant 104 to the skin 508.

Figure 5F:
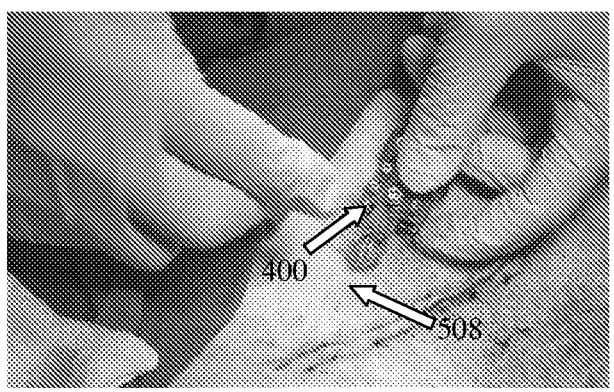

As seen in FIG. 5F (which illustrates removal of the delivery device 400), the skin 508 on top of the distal end of the access device 104 may be held by a tool (not shown in FIG. 5F) and the delivery device 400 may be removed by depressing slightly.

Figure 5G:
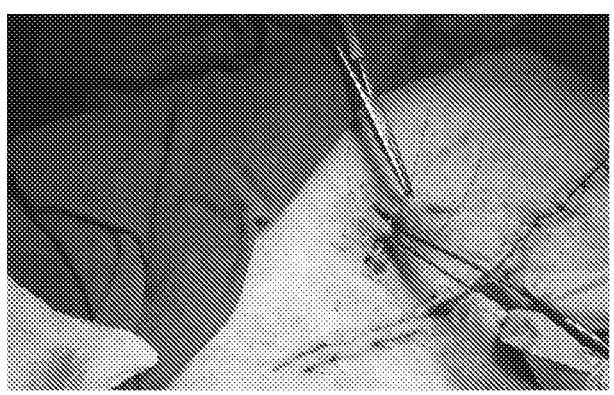

As seen in FIG. 5G (which illustrates closure of the cut-down incision), the incision site may be sutured closed after the procedure (method) for healing. Suturing to close the incision may be performed manually. Dialysis may be commenced after about 5-14 days of encapsulation after the implant 104 is encapsulated by its surrounding subcutaneous tissue. The skin sutures may be removed at this point if the operator wishes to. Dialysis may be performed as described above.

Figure 6C:
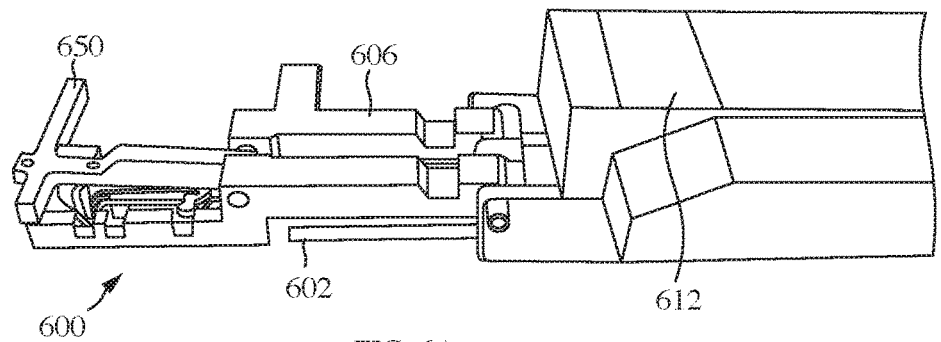
FIG. 6C shows schematic drawings (plan view, side view, and perspective view) illustrating the subcutaneous implant delivery device of FIG. 6A and its components, in accordance with various embodiments.
Figure 6C:
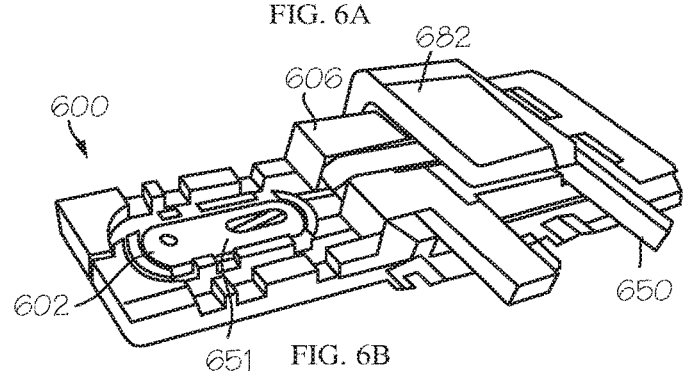
Figure 6C:
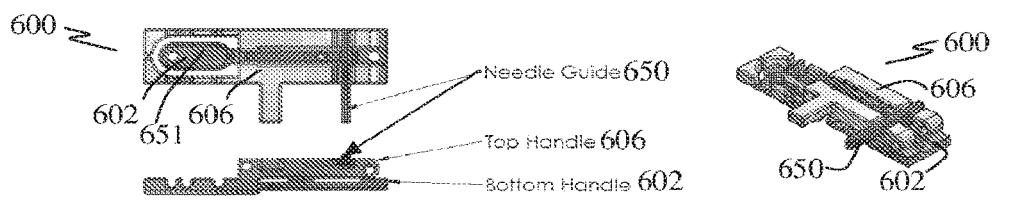
Figure 6C:
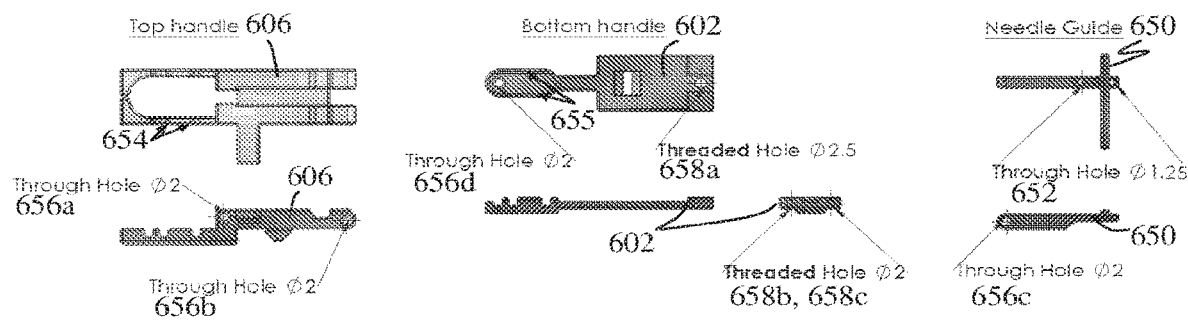

FIG. 6A shows a perspective view of a subcutaneous implant delivery device 600, in accordance with various embodiments, wherein the delivery device 600 may provide guided suturing, guided implant orientation test channels, and additional AV fistula safety of a protection base plate. For example, the subcutaneous implant delivery device 600 may be a subcutaneous implant delivery device, with advance implant orientation guide and AVF safety protection base. In FIG. 6A, a needle guide 650 of the subcutaneous implant delivery device 600 may be positioned over an area of a bottom handle member 602 which is arranged to hold a subcutaneous implant (not shown). The subcutaneous implant delivery device 600 may include a handle 612 that allows an operator to hold on to the subcutaneous implant delivery device 600. FIG. 6B shows a perspective view of the subcutaneous implant delivery device 600 (without the handle 612) where the needle guide 650 is positioned over a top handle 606 of the subcutaneous implant delivery device 600, away from the area where the subcutaneous implant is being held. A U-lock or U-clamp 682 may be provided overlying the needle guide 650 or at least part of the needle guide 650. FIG. 6C shows schematic drawings (plan view, side view, and perspective view) illustrating the subcutaneous implant delivery device 600 of FIG. 6A and its components. For example, the subcutaneous implant delivery device 600 and the subcutaneous implant may include the same or like elements or components as those of the subcutaneous implant delivery apparatus 100 and the subcutaneous implantable device 104 of FIG. 1A, respectively, and as such, the same numerals are assigned and the like elements may be as described in the context of the subcutaneous implant delivery apparatus 100 and the subcutaneous implantable device 104 of FIG. 1A, and therefore the corresponding descriptions may be omitted here.

The delivery device 600 in FIG. 6A may be similar to the simplified version in FIGS. 2A to 2C, but with more features. The delivery device 600 may include the top handle member 606 that acts as a stabilizer, the bottom handle member 602 that holds the subcutaneous implant in place, the needle guide member 650 that guides a test needle (not shown) to verify the correct orientation and position of the subcutaneous implant, and the handle 612. Each of these member (component) may be made from metal, such as though not limited to stainless steel S316, medical grade titaniumetc; and/or from rigid plastics, such as though not limited to polyvinyl chloride (PVC), polycarbonate, acrylonitrile butadiene styrene (ABS), and so on.

The top handle 606 and the bottom handle 602 may function in the same way or in a similar way as the top stabilizer 206 and the bottom holder 202 respectively, as disclosed in FIG. 2A. For example, the bottom handle 602 and the top handle 606 may also include the same or like elements or components as those of the receiving portion 102 and the stabilizing portion 106 of the subcutaneous implant delivery apparatus 100 of FIG. 1A, respectively, and therefore the corresponding descriptions may be omitted here.

As seen in FIGS. 6A to 6C, the bottom handle 602 may hold an access device (e.g., the subcutaneous implant or the subcutaneous implantable device 104 of FIG. 1A). The bottom handle 602 may also be designed with a flat and fully covered hard base 651 (e.g., the protection base plate). The base 651 may be designed to shield the AV fistula or other vasculature/important anatomy that is below the delivery device 600 during the implantation procedure from injury such as misjudged needling or suturing that may puncture/perforate the AV fistula, causing undetected bleeding.

The distal end of the bottom handle 602 may also be configured to include a lowered step (not shown) for holding the subcutaneous implant in place, but yet may allow for easy removal of the delivery device 600 once subcutaneous implant is sutured onto the skin.

The needle guide 650 may be coupled movably to the top handle 606 and may have at least one test-needle throughhole channel(s) 652 which guide the piercing of a small needle size vertically (e.g., 25 G) to ensure the orientation of the access device to access the AV fistula. The device orientation may be confirmed upon seeing blood flash back in the test needle. A plurality of said test-needle channels 652 may be configured along the longitudinally axis of the needle guide 650, for example, the most distal channel leading a test needle to access the AV fistula in the distal front of the subcutaneous implant, the middle channel(s) leading a test needle to access the AV fistula through the subcutaneous implant, and the most proximal channel leading a test needle to access the AV fistula outside the proximal rear of the subcutaneous implant. The configuration of the test needle channels may be designed to verify whether the subcutaneous implant is anchored above a bending AV fistula; and if so, confirming that the subcutaneous implant may still guide any access needle/instruments to access the bending AV fistula.

The top handle 606 may include one or more suture guide groove-markings 654 that guides and confirms an operator has made sutures passing fully through the implant before being anchored onto the skin. For example, the top handle 606 may include at least three suture guide groove-markings. Suture guides 655 may be located on the sides of the bottom handle 602, aligned directly opposite each other to enable a suture needle entering from one side of the implant to exit from the direct opposite position of the other side of the implant horizontally. The top handle 606 may include a first through hole 656a of about 2 mm in diameter, about which the needle guide 650 may be pivoted when aligned with a through hole 656c, and a second through hole 656b of about 2 mm in diameter, about which the handle 612 may be pivoted.

Similar to the top stabilizer 206 of the embodiment in FIG. 2A, the top handle 606 may include a gap at the distal end to ensure the device 600 holds down on the skin firmly but gently for different patients of different skin thickness.

The bottom handle 602 may be fixed to the handle 612 using screws through threaded holes 658a, 658b, 658c of the bottom handle 602.

The through hole 656d at the bottom handle 602 may be the access hole for a test needle (e.g., 734 of FIG. 7C) which allows the test needle to pass through the bottom handle 602 during the device orientation flashback testing.

The handle 612 may be configured to be attached to proximal ends of the top handle 606, the bottom handle 602 and the needle guide 650 to allow the operator to hold on to the delivery device 600.

Figure 6D:
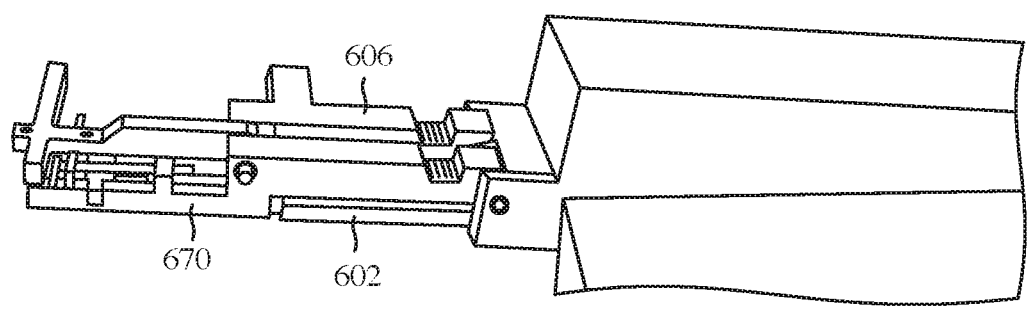
FIG. 6D shows a perspective view of a subcutaneous implant delivery device, which is a similar variation of the subcutaneous implant delivery device of FIG. 6A, with added quick implant release mechanism, in accordance with various embodiments.
Figure 6E:
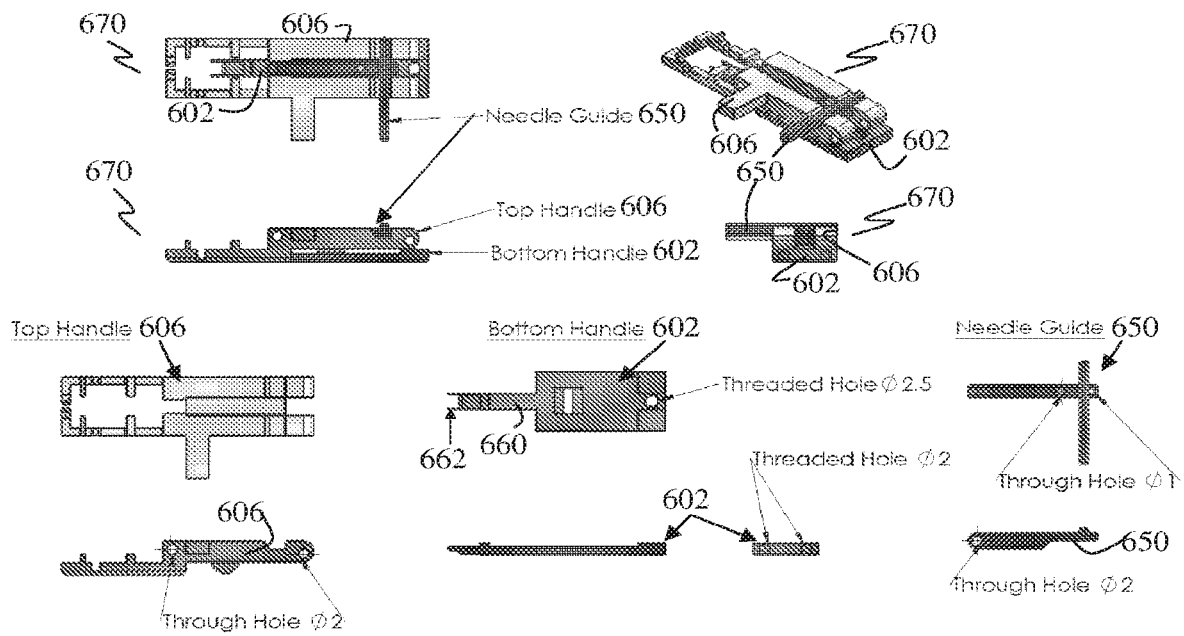
FIG. 6E shows schematic drawings (plan view, side view, and perspective view) illustrating the subcutaneous implant delivery device of FIG. 6D and its components, in accordance with various embodiments.

FIG. 6D shows a perspective view of a subcutaneous implant delivery device 670, which is a similar variation of the subcutaneous implant delivery device 600 of FIG. 6A, with added quick implant release mechanism. In other words, the device 670 of FIG. 6D is somewhat similar to or based on that of FIG. 6A, with some variations. For example, the subcutaneous implant delivery device 670 may have advance implant orientation guide, AVF safety protection base and implant quick release features. For convenience of referencing, the subcutaneous implant delivery device 600 of FIG. 6A and the subcutaneous implant delivery device 670 of FIG. 6D may have the same or like elements or components, and as such, the same numerals are assigned and the like elements may be as described in the context of subcutaneous implant delivery device 600 of FIG. 6A, and therefore the corresponding descriptions may be omitted here. FIG. 6E shows schematic drawings (plan view, side view, and perspective view) illustrating the subcutaneous implant delivery device 670 of FIG. 6D and its components.

As seen in FIGS. 6D and 6E, one additional feature may be a quick release mechanism located at the bottom handle member 602 of the device 670. Instead of a protection base plate (e.g., 651 of FIG. 6B) and a side surrounding step to hold a subcutaneous implant in place, the bottom handle 602 may include a shaft 660 with a distal end of a male socket 662. The male socket 662 may be designed with pings that slip fits a female (complementary) socket (not shown) on the subcutaneous implant to hold the implant in place. The male socket 662 may enable the delivery device 670 to quick release the subcutaneous implant when the implantation procedure is completed.

For the quick release version of the delivery device 670 of FIG. 6D, the delivery device 670 may be removed by simply pulling the delivery device 670 out, with the male slip fit socket 662 releasing the subcutaneous implant or the access device (e.g., 104 of FIG. 1A) that is anchored under the skin.

In other example, the bottom handle 602 may include a shaft 660 with a distal end of a female socket, which may slip fit to a male socket on the subcutaneous implant to hold the implant in place.

Figure 6F:
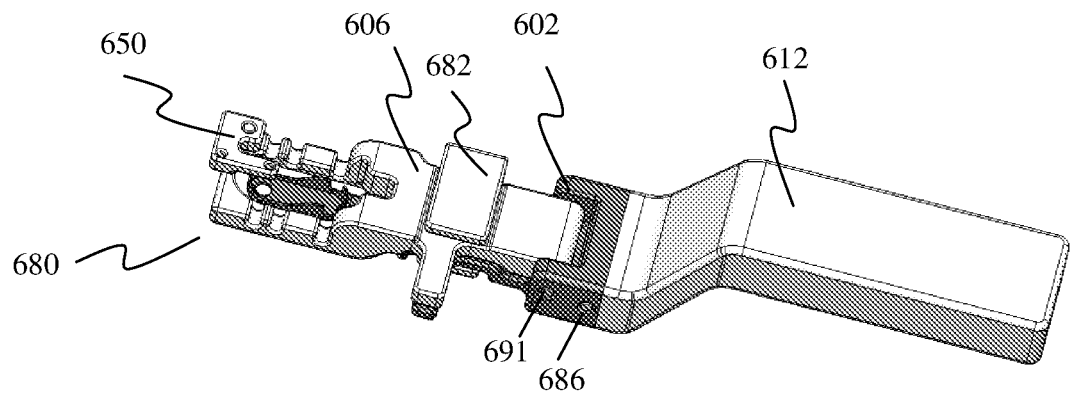
FIG. 6F shows a perspective view of another subcutaneous implant delivery device, which is a similar variation of the subcutaneous implant delivery device of FIG. 6A, with improved design and fastening mechanism, in accordance with various embodiments.
Figure 6G:
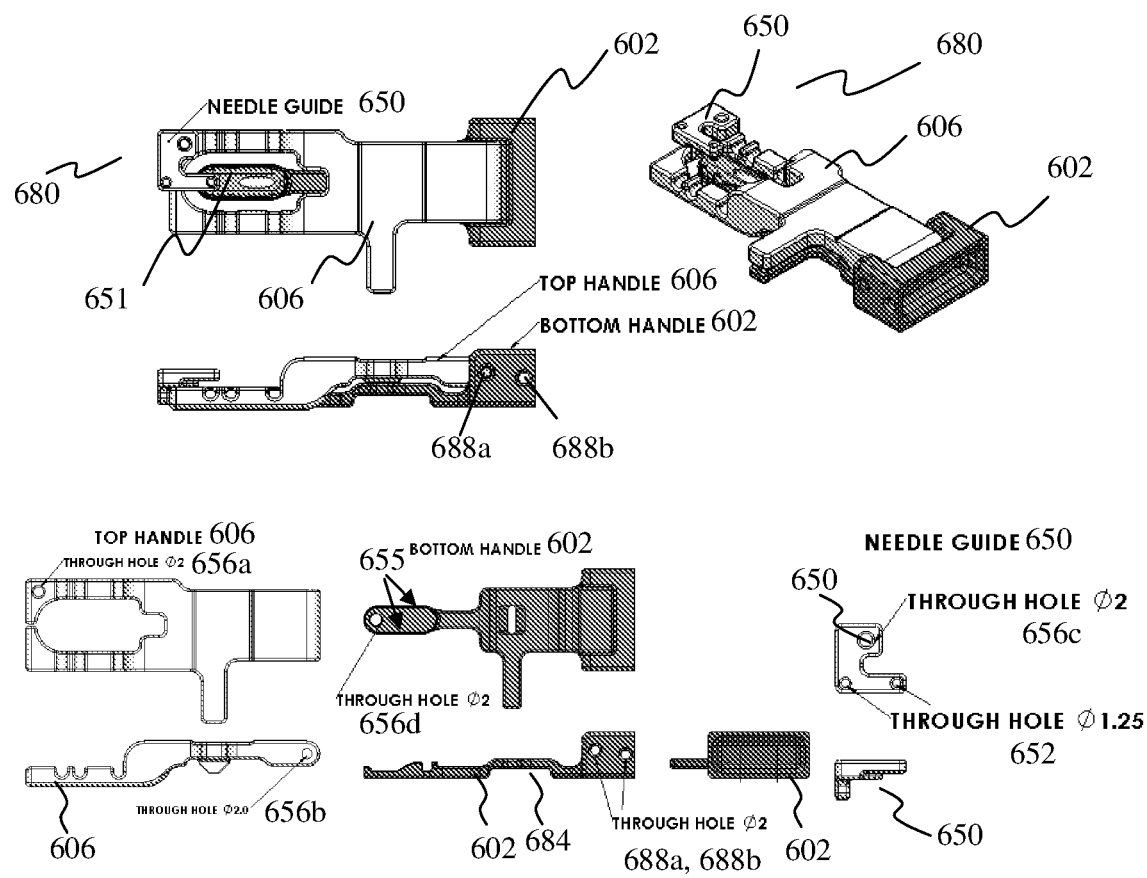
FIG. 6G shows schematic drawings (plan view, side view, and perspective view) illustrating the subcutaneous implant delivery device of FIG. 6F and its components, in accordance with various embodiments.

FIG. 6F shows a perspective view of another subcutaneous implant delivery device 680, which is a similar variation of the subcutaneous implant delivery device 600 of FIG. 6A, with improved design and fastening mechanism. In other words, the device 680 of FIG. 6F is somewhat similar to or based on that of FIG. 6A, with some variations. For convenience of referencing, the subcutaneous implant delivery device 600 of FIG. 6A and the subcutaneous implant delivery device 680 of FIG. 6F may have the same or like elements or components, and as such, the same numerals are assigned and the like elements may be as described in the context of subcutaneous implant delivery device 600 of FIG. 6A, and therefore the corresponding descriptions may be omitted here. FIG. 6G shows schematic drawings (plan view, side view, and perspective view) illustrating the subcutaneous implant delivery device 680 of FIG. 6F and its components. For the variation of the subcutaneous implant delivery device 680 (FIG. 6F), four features may be modified as improvements to the device 600 of FIG. 6A. For example, the four improved features may be:— a) Lateral swing activated needle guide—In the device 600 (FIG. 6A), the needle guide 650 may be mounted on the top handle 606, pivoted to the through hole 656a and activated by rotation about the pivot. For the subcutaneous implant delivery device 680 (FIG. 6F), the needle guide 650 may be mounted on the top handle 606, pivoted to a lateral through hole 656a and activated by swing rotation. This modification may provide an advantage of not needing the U-clamp 682 to be removed and reinserted when a test needle (e.g., 734 of FIG. 7C) is deployed through the needle guide 650, over the course of the procedure as outlined in FIGS. 7A to 7H. In other words, the use of the subcutaneous implant delivery device 680 (FIG. 6F) may further simplify the procedure.

b) Skin-pinching prevention groove for U-clamp—As illustrated in FIG. 6G, a groove 684 may be created on the bottom handle 602. The purpose of the groove 684 may be to allow the U-clamp 682 to flush with the bottom surface of the bottom handle 602, thereby preventing skin from being pinched when the U-clamp 682 is engaged to lock the top handle 606 and the bottom handle 602 together.

c) Shorter handle—The subcutaneous implant delivery device 680 may differ from the device 600 by having a shorter handle (e.g., 612, FIG. 6F). This may reduce the weight of the device 680, provide better balance, improve user comfort and reduce manufacturing cost.

d) Screwless hinges—In the device 600 (FIG. 6A), three screws for the screws through threaded holes 658a, 658b, and 658c (FIG. 6C) may be used to attach the handle 612 to the bottom handle 602. In the subcutaneous implant delivery device 680 (FIG. 6F), the three screws (FIG. 6C) may be replaced by one threadless press fit rod hinge 686 (FIG. 6F) passes through the through hole 688b in FIG. 6G. The purpose of replacing screws (as in the device 600 of FIG. 6A) with a threadless press fit rod hinge (as in the subcutaneous implant delivery device 680 of FIG. 6F) may be to reduce risk of residual sterilization ethylene oxide (EtO) entrapped in the screw threads. This improvement/modification may enable the sterilization process to be easier. In the device 600, the top handle 606 may be attached to the handle 612 with a press fit rod hinge (e.g., through the through hole 656b of FIG. 6C), but in the subcutaneous implant delivery device 680 of FIG. 6F, the top handle 606 may be attached to the bottom handle 602 with a press fit rod hinge 691 in FIG. 6F that passes through the through hole 656b (FIG. 6G) and through hole 688a (FIG. 6G).

FIGS. 7A to 7H show diagrams illustrating a method of utilizing the delivery device 600 of FIG. 6A and/or the variation thereof (i.e., the delivery device 680 of FIG. 6F) to implant a subcutaneous implant, such as a vascular access device for AV fistula.

Figure 7A:
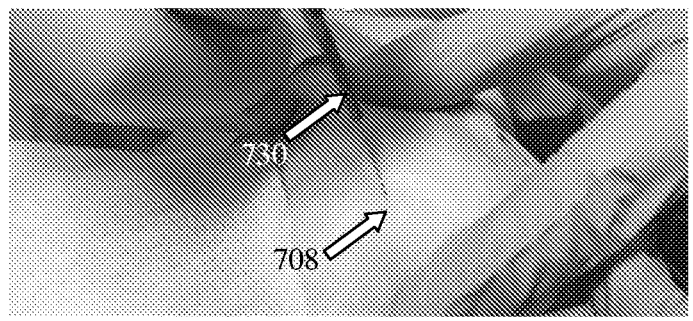
FIGS. 7A to 7H show diagrams illustrating a method of utilizing the delivery device of FIG. 6A or the variation thereof (i.e., the delivery device of FIG. 6F) to implant a subcutaneous implant, such as a vascular access device for arteriovenous fistula (AVF or AV fistula), in accordance with various embodiments.

As seen in FIG. 7A which illustrates creating an incision, a cut down incision between about 1 cm to about 3 cm long may be created on a skin 708. The incision may be created using a surgical knife 730. The incision may allow access to a space below the dermis and a thin layer of subcutaneous tissue. A tunnel along the subcutaneous tissue under the skin 708 may be created. The tunnel may be about 2-3 mm below the top surface of the skin 708 (or about 1 mm below the bottom layer of the skin 708), running parallel with the AV fistula in a longitudinal direction.

Figure 7B:
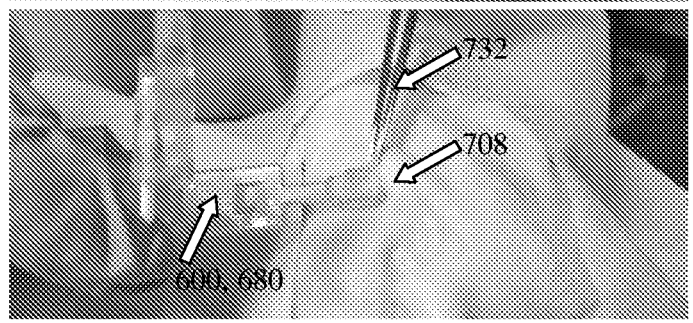

As seen in FIG. 7B (which illustrates insertion of an implant), an access device (e.g., the subcutaneous implantable device 104 of FIG. 1A) may be inserted using the delivery device 600, 680 into the incision created, and slipped along and into the subcutaneous tissue tunnel in the longitudinal direction parallel with the AVF. The depth of insertion may depend on the incision created or until the depth as indicated by the delivery device 600, 680. A forcep or tweezer 732 may be used to hold the skin 708 and assist the insertion of the delivery device 600, 680.

Figure 7C:
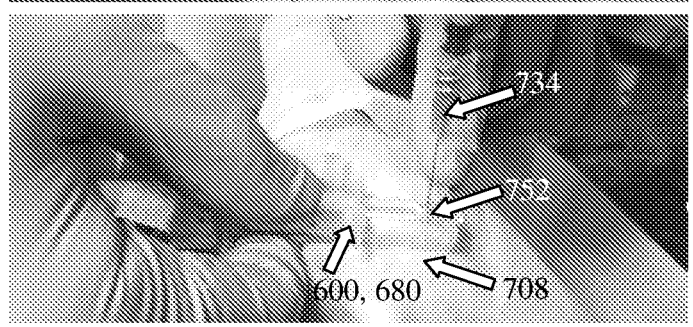

The orientation of the access device 104 (that is hidden underneath the skin 708) may be confirmed by using a test needle 734, which may be smaller in size than a typical dialysis needle (such as 21 G to 25 G), to access the AV fistula as seen in FIG. 7C (which illustrates confirmation of implant orientation). The device orientation may be confirmed upon seeing blood flash back in the test needle 734. The test needle 734 may be inserted at an angle perpendicular to the implant 104 along needle guide test channels 752. For example, the test needle 734 may be used on every of the two needle guide channels 752, to access the AV fistula in front of, through and/or behind the access device 104. This two test checks may verify whether the implanted access device 104 is positioned above an AV fistula at a bend, and if so, may be able to guide a needle (not shown in FIG. 7C) to access a curved AV fistula successfully.

Figure 7D:
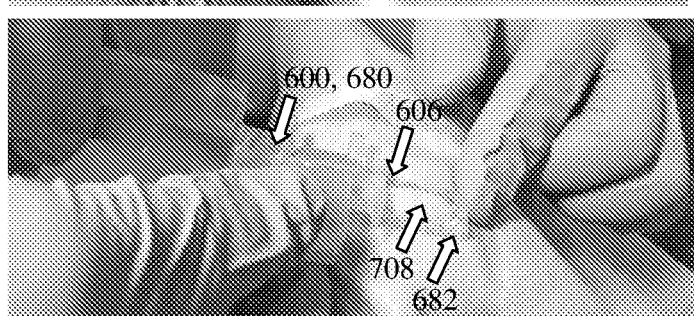

Upon confirmation of the correct position and orientation of the access device 104, the top handle 606 and the bottom handle 602 (not shown) of the delivery device 600, 680 may be locked in place with a U-lock 682, sandwiching the skin 708 and the access device 104 together, as seen in FIG. 7D (which illustrates locking of the device 600, 680 in place using the U-lock 682). The U-lock 682 may temporarily lock the access device 104 in a fixed position relative to the skin 708 and the AV fistula.

Figure 7E:
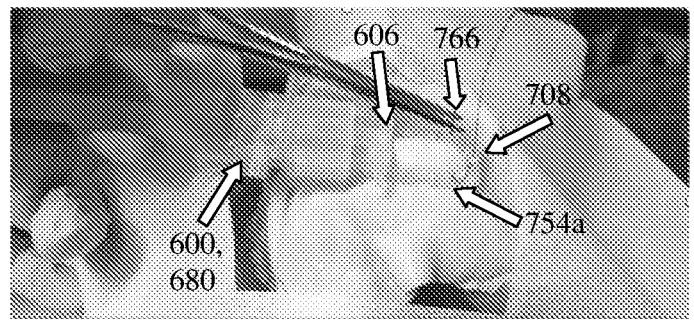

As seen in FIG. 7E (which illustrates suturing the distal end of the access device 104), the distal end of the implanted access device 104 may be sutured onto the skin 708. A suture needle 766 may be passed through suture guide groove-markings 754a (found on both sides of the top handle 606) that guide and confirm the operator has made sutures passing fully through the access device 104. Upon this confirmation, the sutures may be tightened to pull the access device 104 upwards and tied to securely anchor the implant 104 against the skin 708.

Figure 7F:
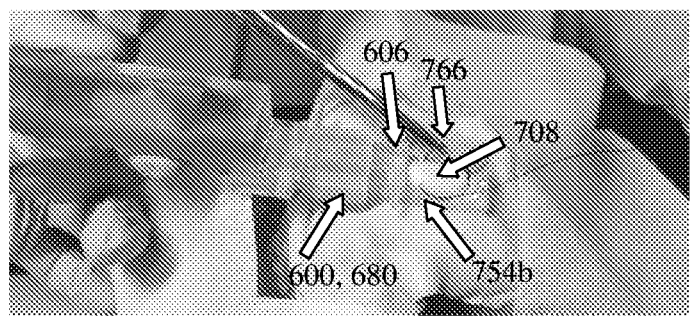

As seen in FIG. 7F (which illustrates suturing the proximal end of the access device 104), the proximal end of the implanted access device 104 may be sutured onto the skin 708. The suture needle 766 may be passed through suture guide groove-markings 754b (found on both sides of the top handle 606) that guide and confirm the operator has made sutures passing fully through the access device 104. Upon this confirmation, the sutures may be tightened to pull the access device 104 upwards and tied to securely anchor the implant 104 against the skin 708.

Figure 7G:
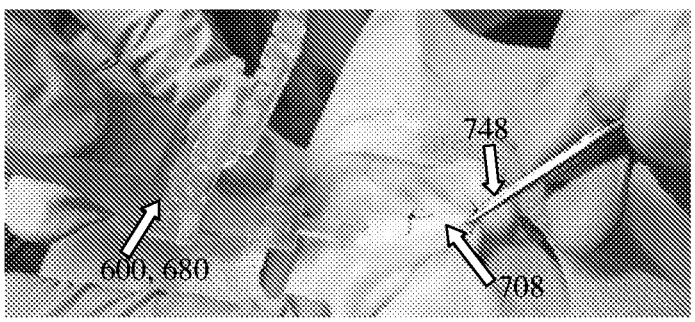

FIG. 7G illustrates removal of the delivery device 600, 680. For the version of the delivery device 600, 680 of FIG. 6A and FIG. 6F, the skin 708 on top of the distal end of the access device 104 may be held by a tool 748 (e.g., a forcep or a tweezer) and the delivery device 600 may be removed by depressing slightly.

Figure 7H:

As seen in FIG. 7H (which illustrates closure of the incision), the incision site may be sutured closed after the procedure (method) for healing. Dialysis may be commenced after about 5-14 days, after the implant 104 is encapsulated by its surrounding subcutaneous tissue. The skin sutures may be removed at this point if the operator wishes to. Once dialysis is completed, a needle for dialysis may be removed and pressure may be applied on the area to achieve hemostasis as per usual work protocol. As seen in FIGS. 7E, 7F and 7H, suturing may be performed manually.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A subcutaneous implant delivery apparatus comprising:
   a receiving portion configured to receive a subcutaneous implantable device; and
   a stabilizing portion configured to cooperate with the receiving portion to hold the subcutaneous implantable device in a fixed position with a skin layer between the receiving portion and the stabilizing portion,
   wherein the receiving portion and the stabilizing portion are movable relative to each other between a released configuration and a closed configuration;
   wherein in the released configuration, the receiving portion and the stabilizing portion are configured to move apart from each other to allow the receiving portion to be inserted under the skin layer and the subcutaneous implantable device to be positioned subcutaneously maintaining the skin layer between the receiving portion and the stabilizing portion; and
   wherein in the closed configuration, the receiving portion and the stabilizing portion are configured to move toward each other maintaining the skin layer between them to allow the subcutaneous implantable device to be held adjacent to the skin layer, between the receiving portion and the stabilizing portion, in the fixed position.

2. The subcutaneous implant delivery apparatus of claim 1, further comprising at least one position indicator configured to facilitate a visual indication of at least one of a position or an angular orientation of the subcutaneous implantable device when received by the receiving portion and held adjacent to the skin layer.

3. The subcutaneous implant delivery apparatus of claim 2, wherein the position indicator comprises a needle guide configured to receive a needle upon alignment of the subcutaneous implantable device to at least one of a desired position or a desired angular orientation with respect to the receiving portion.

4. The subcutaneous implant delivery apparatus of claim 3, wherein the needle guide is configured to be coupled to the stabilizing portion and activated by a swing rotation to move laterally along the stabilizing portion.

5. The subcutaneous implant delivery apparatus of claim 1, further comprising at least one anchor guide configured to facilitate the subcutaneous implantable device to be anchored to the skin layer.

6. The subcutaneous implant delivery apparatus of claim 5, wherein the at least one anchor guide comprises a suture guide marking.

7. The subcutaneous implant delivery apparatus of claim 1, wherein the receiving portion comprises a blocking base plate on which the subcutaneous implantable device is to be placed, wherein the blocking base plate is configured to form a shield for an anatomy or a tissue underneath the subcutaneous implantable device.

8. The subcutaneous implant delivery apparatus of claim 1, wherein the receiving portion comprises a releasable attachment mechanism to which the subcutaneous implantable device is to be releasably attached.

9. The subcutaneous implant delivery apparatus of claim 1, wherein the receiving portion and the stabilizing portion are movable relative to each other about a pivoting point.

10. The subcutaneous implant delivery apparatus of claim 1, further comprising a handle extending from at least one of the receiving portion or the stabilizing portion.

11. The subcutaneous implant delivery apparatus of claim 10, wherein the handle is made of plastic.

12. The subcutaneous implant delivery apparatus of claim 1, further comprising a handle extending from each of the receiving portion and the stabilizing portion.

13. The subcutaneous implant delivery apparatus of claim 12, wherein the handles are configured to move toward each other upon exerting an external force thereon to correspondingly allow the receiving portion and the stabilizing portion to be moveable toward each other in the closed configuration.

14. The subcutaneous implant delivery apparatus of claim 1, further comprising at least one needle arranged to self suture through the subcutaneous implantable device when received by the receiving portion, to the skin layer upon moving the receiving portion and the stabilizing portion toward each other.

15. The subcutaneous implant delivery apparatus of claim 1, wherein the receiving portion and the stabilizing portion are made of a material selected from plastic, austenitic molybdenum-containing stainless steel, and medical grade titanium.

16. The subcutaneous implant delivery apparatus of claim 1, further comprising a locking mechanism arranged to releasably lock the receiving portion and the stabilizing portion in the closed configuration.

17. The subcutaneous implant delivery apparatus of claim 16, wherein each of the receiving portion and the stabilizing portion comprises a screw hole, and wherein the locking mechanism comprises a screw arranged through the screw holes.

18. The subcutaneous implant delivery apparatus of claim 16, wherein the locking mechanism comprises a U-lock or a U-clamp.

19. A method of delivering a subcutaneous implantable device for accessing a vascular site, the method comprises:
   providing a subcutaneous implant delivery apparatus of claim 1;
   receiving a subcutaneous implantable device on the receiving portion of the subcutaneous implant delivery apparatus;
   inserting the receiving portion under a skin layer;
   positioning the subcutaneous implantable device subcutaneously;
   holding the subcutaneous implantable device adjacent to the skin layer between the receiving portion and the stabilizing portion in a fixed position;
   releasing the subcutaneous implantable device by allowing the receiving portion and the stabilizing portion to move apart from each other; and
   removing the receiving portion from under the skin layer.

20. The method of claim 19, further comprising providing a blocking base plate on which the subcutaneous implantable device is to be placed to form a shield for an anatomy or a tissue underneath the subcutaneous implantable device.

\* \* \* \* \*